(12) United States Patent
Nathan

(10) Patent No.: US 11,072,657 B2
(45) Date of Patent: Jul. 27, 2021

(54) TREATMENT OF LUNG CANCER USING A COMBINATION OF AN ANTI-PD-1 ANTIBODY AND AN ANTI-CTLA-4 ANTIBODY

(71) Applicant: Bristol-Myers Squibb Company, Princeton, NJ (US)

(72) Inventor: Faith Nathan, Moorestown, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 392 days.

(21) Appl. No.: 15/776,732

(22) PCT Filed: Nov. 18, 2016

(86) PCT No.: PCT/US2016/062884
§ 371 (c)(1),
(2) Date: May 16, 2018

(87) PCT Pub. No.: WO2017/087870
PCT Pub. Date: May 26, 2017

(65) Prior Publication Data
US 2018/0371092 A1 Dec. 27, 2018

Related U.S. Application Data

(60) Provisional application No. 62/257,139, filed on Nov. 18, 2015, provisional application No. 62/345,314, filed on Jun. 3, 2016.

(51) Int. Cl.
*C07K 16/28* (2006.01)
*A61K 39/395* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *A61K 2039/507* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 5,977,318 A | 11/1999 | Linsley et al. | |
| 6,051,227 A | 4/2000 | Allison et al. | |
| 6,682,736 B1 | 1/2004 | Hanson et al. | |
| 6,808,710 B1 | 10/2004 | Wood et al. | |
| 6,984,720 B1 | 1/2006 | Korman et al. | |
| 7,034,121 B2 | 4/2006 | Carreno et al. | |
| 7,488,802 B2 | 2/2009 | Collins et al. | |
| 7,595,048 B2 | 9/2009 | Honjo et al. | |
| 7,605,238 B2 | 10/2009 | Korman et al. | |
| 7,943,743 B2 | 5/2011 | Korman et al. | |
| 8,008,449 B2 | 8/2011 | Korman et al. | |
| 8,168,179 B2 | 5/2012 | Honjo et al. | |
| 8,168,757 B2 | 5/2012 | Finnefrock et al. | |
| 8,217,149 B2 | 7/2012 | Irving et al. | |
| 8,354,509 B2 | 1/2013 | Carven et al. | |
| 8,609,089 B2 | 12/2013 | Langermann et al. | |
| 8,728,474 B2 | 5/2014 | Honjo et al. | |
| 8,779,105 B2 | 7/2014 | Korman et al. | |
| 8,779,108 B2 | 7/2014 | Queva et al. | |
| 8,900,587 B2 | 12/2014 | Carven et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,212,224 B2 | 12/2015 | Cogswell et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 9,856,320 B2 * | 1/2018 | Cogswell | ............... A61P 35/00 |
| 10,072,082 B2 | 9/2018 | Cogswell et al. | |
| 2011/0081354 A1 * | 4/2011 | Korman | ............. A61K 39/3955 424/152.1 |
| 2012/0263677 A1 | 10/2012 | Eagle et al. | |
| 2013/0017199 A1 | 1/2013 | Langermann | |

(Continued)

FOREIGN PATENT DOCUMENTS

| | | |
|---|---|---|
| WO | WO-2007113648 A2 | 10/2007 |
| WO | WO-2012122444 A1 | 9/2012 |

(Continued)

OTHER PUBLICATIONS

Bagley et al. (2015) Clinical Advances in Hematology & Oncology, 13: 676-683.*
Bagley et al. (2015) The New England Journal of Medicine, 372: 2018-2028.*
Antonia, S.J., et al., "Safety and Efficacy of First-Line nivolumab (Anti-PD-1; BMS-936558, ONO-4538) and Ipilimumab in Non-Small Cell Lung Cancer (NSCLC) Metastatic Non-Small CellLung Cancer (NSCLC) Metastatic non-small Cell Lung Cancer," International Journal of Radiation:Oncology Bio Physics 90(5): s32-s33, Abstract Elsevier, Netherlands (Nov. 15, 2014).
ASCO 2015 Special Issue: Magazine of European Medical Oncology vol. 8 (3): 53-70. (Nov. 3, 2015).
Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).

(Continued)

*Primary Examiner* — Ilia I Ouspenski
(74) *Attorney, Agent, or Firm* — Sterne, Kessler, Goldstein & Fox P.L.L.C.

(57) ABSTRACT

This disclosure provides a method for treating a subject afflicted with a lung cancer, which method comprises administering to the subject therapeutically effective amounts of: (a) an antibody or an antigen-binding portion thereof that specifically binds to a Programmed Death-1 (PD-1) receptor and inhibits PD-1 activity; and (b) an antibody or an antigen-binding portion thereof that specifically binds to a Cytotoxic T-Lymphocyte Antigen-4 (CTLA-4) and inhibits CTLA-4 activity.

11 Claims, 8 Drawing Sheets

(56) References Cited

U.S. PATENT DOCUMENTS

| | | | |
|---|---|---|---|
| 2014/0212422 A1* | 7/2014 | Korman | A61K 39/3955 424/135.1 |
| 2014/0341917 A1 | 11/2014 | Nastri et al. | |
| 2014/0356353 A1 | 12/2014 | Queva et al. | |
| 2015/0079109 A1 | 3/2015 | Li et al. | |
| 2015/0190505 A1* | 7/2015 | Yeung | A61K 39/235 424/135.1 |
| 2015/0283234 A1* | 10/2015 | Graziano | A61P 35/00 424/139.1 |
| 2016/0060343 A1* | 3/2016 | Huang | A61P 35/00 424/142.1 |
| 2016/0362489 A1* | 12/2016 | Yang | C07K 16/2818 |
| 2017/0051060 A1 | 2/2017 | Honjo et al. | |
| 2017/0088615 A1 | 3/2017 | Korman et al. | |
| 2017/0158776 A1* | 6/2017 | Feltquate | A61K 33/24 |
| 2017/0274074 A1* | 9/2017 | Das-Young | A61K 39/39558 |
| 2017/0281767 A1* | 10/2017 | Chang | A61K 39/39558 |
| 2018/0117092 A1* | 5/2018 | Naughton | C12N 5/0652 |
| 2018/0155429 A1 | 7/2018 | Finckenstein | |
| 2018/0273624 A1 | 9/2018 | Cogswell et al. | |
| 2018/0319892 A1* | 11/2018 | Feltquate | A61K 33/24 |
| 2019/0292260 A1* | 9/2019 | Tschaika | A61P 43/00 |

FOREIGN PATENT DOCUMENTS

| | | |
|---|---|---|
| WO | WO-2012145493 A1 | 10/2012 |
| WO | WO-2013173223 A1 | 11/2013 |
| WO | WO-2015070060 A1 | 5/2015 |
| WO | WO-2015176033 A1 | 11/2015 |
| WO | WO-2016191751 A1 | 1/2016 |
| WO | WO-2017087870 A1 | 5/2017 |
| WO | WO-2017132508 A1 | 8/2017 |
| WO | WO-2017176925 A1 | 10/2017 |
| WO | WO-2017210624 A1 | 12/2017 |
| WO | WO-2017210631 A1 | 12/2017 |

OTHER PUBLICATIONS

Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (Jul. 2010).

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).

Creelan, B.C., "Update on Immune Checkpoint Inhibitors in Lung Cancer," Cancer Control: Journal of the Moffitt Cancer Center 21(1):80-89, H. Lee Moffitt Cancer Center and Research Institute, United States (Jan. 2014).

GenBank, "cytotoxic T-lymphocyte-associated protein 4 [Homo sapiens]," Accession No. AAB59385.1, accessed on https://www.ncbi.nlm.nih.gov/protein/AAB59385, Nov. 1, 1994.

GenBank, "Human hPD-1 (hPD-1) mRNA, complete cds," Accession No. U64863.1, accessed on https://www.ncbi.nlm.nih.gov/nuccore/U64863, Oct. 12, 2005.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.

Hanna, N., et al., "Randomized Phase III Trial of Pemetrexed Versus Docetaxel in Patients with Non-small-cell Lung Cancer Previously Treated with Chemotherapy," Journal of Clinical Oncology 22(9):1589-1597, American Society of Clinical Oncology, United States (May 2004).

Herbst, R.S., et al., "A Study of MPDL3280A, an Engineered PD-L1 Antibody in Patients with Locally Advanced or Metastatic Tumors," Journal of Clinical Oncology 31(Suppl):Abstract 3000, American Society of Clinical Oncology, United States (2013).

Hodi, F.S., et al., "Improved Survival with Ipilimumab in Patients with Metastatic Melanoma," The New England Journal of Medicine 363(8):711-723, Massachusetts Medical Society, United States (Aug. 2010).

International Preliminary Report on Patentability for International Application No. PCT/US2016/062884, dated May 22, 2018, 9 pages.

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

McCabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).

NCCN Guidelines® (2014), available at http://www.nccn.org/professionals/physician_gls/f_guidelines.asp, last accessed May 14, 2014, 4 pages.

NCCN Guidelines, Version 3.2014—Non-Small Cell Lung Cancer, available at: http://www.nccn.org/professionals/physician_gls_pdf/nscl.pdf, last accessed May 14, 2014.

NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.

NCI Drug Dictionary, pembrolizumab, accessed on Dec. 1, 2016, retrieved from the Internet URL: https://www.cancer.gov/drugdictionary?cancer-drug?cdrid=695789, 3 pages.

Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).

Phillips, T., et al., "Development of an Automated PD-L1 Immunohistochemistry (IHC) Assay for Non-small Cell Lung Cancer," Applied Immunohistochemistry & Molecular Morphology, 23(8):541-549, Lippincott Williams & Wilkins, United States (Sep. 2015).

Rizvi, N.A., et al., "Nivolumab/Ipilmumab Combination Active in Advanced NSCLC," Presented at 16th World Conference on Lung Cancer, Sep. 6-9, Denver Colorado, retrieved from http://www.onclive.com/printer?url=/conference-coerage/2015-world-lung/nivolumabipilmumab-combination-active-in-advanced-nsclc.

International Search Report and Written opinion for International Application No. PCT/US2016/062884, dated May 26, 2018, 16 pages.

Siegel, R., et al., "Cancer Statistics, 2014," CA: A Cancer Journal for Clinicians 64(1):9-29, Wiley, United States (Jan. 2014).

Sjoblom, T., et al., "The Consensus Coding Sequences of Human Breast and Colorectal Cancers," Science 314(5797):268-274, American Association for the Advancement of Science, United States (Oct. 2006).

Gettinger, S.N., et al., "First-line Monotherapy With Nivolumab (NIVO; Antiprogrammed Death-1 [PD-1]) in Advanced Non-small Cell Lung Cancer (NSCLC): Safety, Efficacy and Correlation of Outcomes With PD-1 Ligand (PD-L1) Expression [abstract]," Journal of Clinical Oncology 33(suppl):8025, (May 20, 2015).

Taube, J.M., et al., "Colocalization of Inflammatory Response with B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).

Taylor, M., et al., Phase I/II study of nivolumab with or without ipilimumab for treatment of recurrent small cell lung cancer (SCLC): CA209-032, Journal for Immunotherapy of Cancer: Biomed Central (3)(2):102, United Kingdom (2015).

Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).

Wang, C., et al., "In Vitro Characterization of the Anti-PD-1 Antibody Nivolumab, BMS-936558, and in Vivo Toxicology in

(56) References Cited

OTHER PUBLICATIONS

Non-human Primates," Cancer Immunology Research 2(9):846-856, American Association for Cancer Research, United States (May 28, 2014).
Wolchok, J.D., et al., "Nivolumab Plus Ipilimumab in Advanced Melanoma," The New England Journal of Medicine 369(2):122-133, Massachusetts Medical Society, United States (Jul. 2013).
Co-pending Application, U.S. Appl. No. 16/073,676, inventor Nathan, F., filed Jan. 27, 2017 (Not Published).
Co-pending Application, U.S. Appl. No. 16/024,376, inventor Nathan, F., filed Jun. 29, 2018 (Not Published).
Co-pending Application, U.S. Appl. No. 16/091,441, inventor Farsaci, B., filed Apr. 5, 2017 (Not Published).
Patel et al., "PD-L1 expression as a predictive biomarker in cancer immunotherapy," *Molecular Cancer Therapeutics* 14(4):847-86 (Feb. 18, 2015).
Garon, et al., "Pembrolizumab for the Treatment of Non-Small-Cell Lung Cancer," *New England Journal of Medicine* 372(21):2018-28 (Apr. 19, 2015).

\* cited by examiner

Figure 1.

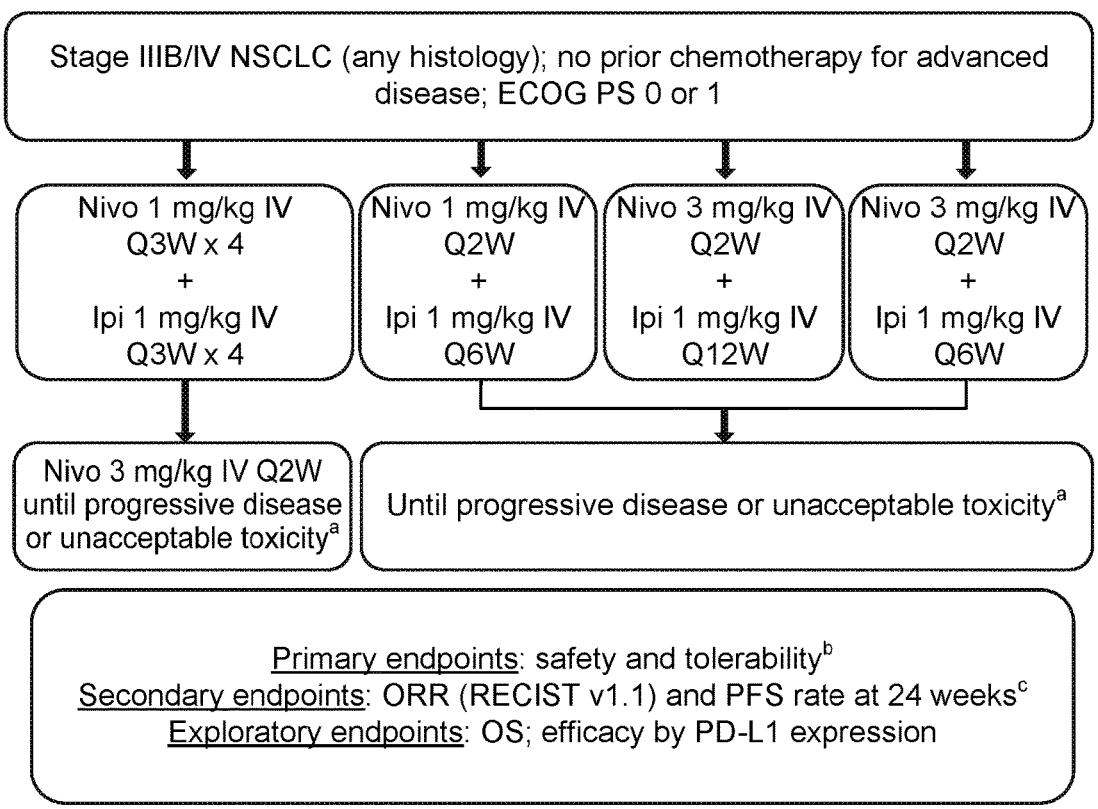

[a]Patients tolerating study treatment were permitted to continue treatment beyond RECIST v1.1-defined progression if considered to be deriving clinical benefit
[b]The severity of AEs was graded using the NCI Common Terminology Criteria for Adverse Events, v4.0
[c]Response was assessed at weeks 10 (nivo 1 + ipi 1 Q3W) or 11 (nivo 1 Q2W + ipi 1 Q6W; nivo 3 Q2W + ipi 1 Q12W or Q6W), 17, and 23, and every 3 months thereafter until disease progression
PFS = progression-free survival ✢ First occurrence of new lesion  ☐ % change truncated to 100%

Includes all patients with baseline target lesion and ≥1 post-baseline assessment of target lesion
Horizontal lines denote 30% decrease, no change, and 20% increase Includes all patients with baseline target lesion and ≥1 post-baseline assessment of target lesion. Positive change in tumor burden indicates tumor growth; negative change in tumor burden indicates tumor reduction. Not all reductions of ≥30% from baseline are partial responses
[a]Based on patients with known PD-L1 expression (n = 113); [b]Based on all treated patients (n = 148)

PD = progressive disease; SD = stable disease
Includes all patients with baseline target lesion and ≥1 post-baseline assessment of target lesion (n = 33)
Horizontal lines denote 30% decrease, no change, and 20% increase

FIG. 7A
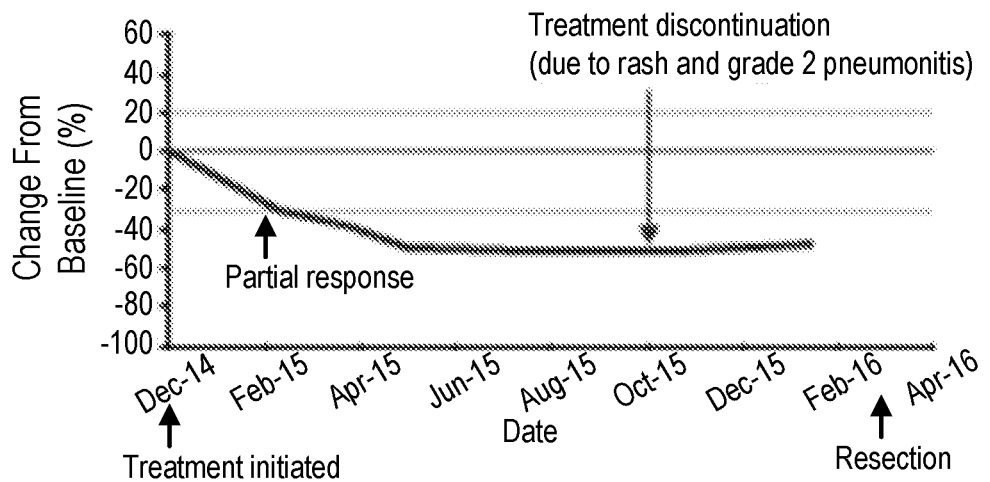
FIG. 7B
Before nivo + Ipi therapy
FIG. 7C
Following nivo + Ipi therapy
FIG. 7D
No viable tumor in resected residual lesion
Right upper lobe wedge resection (nodule #1) Mar-2016
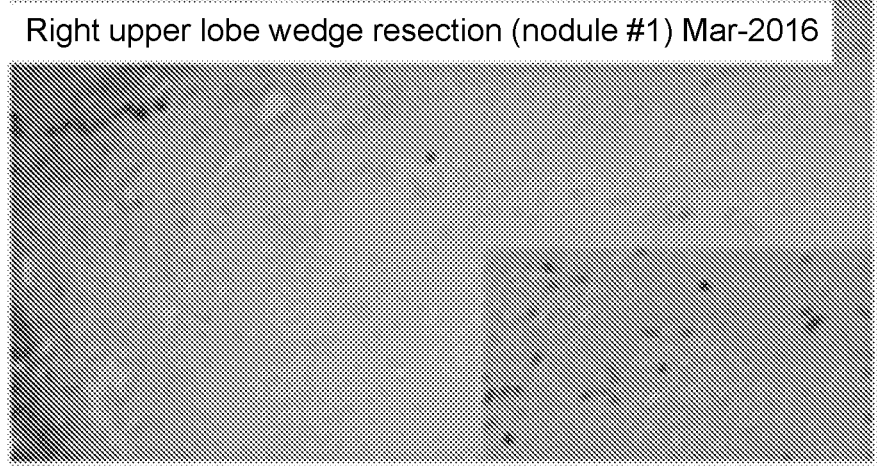

TREATMENT OF LUNG CANCER USING A COMBINATION OF AN ANTI-PD-1 ANTIBODY AND AN ANTI-CTLA-4 ANTIBODY

FIELD OF THE INVENTION

This invention relates to methods for treating lung cancer in a subject comprising administering to the subject a combination of an anti-Programmed Death-1 (PD-1) antibody and an anti-Cytotoxic T-Lymphocyte Antigen-4 (CTLA-4) antibody.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down-regulate T cell activation and cytokine secretion upon binding to PD-1.

Nivolumab (formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

Ipilimumab (YERVOY®) is a fully human, IgG1 monoclonal antibody that blocks the binding of CTLA-4 to its B7 ligands, thereby stimulating T cell activation and improving overall survival (OS) in patients with advanced melanoma (Hodi et al. (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al. (2013) *N Engl J Med* 369(2):122-33; WO 2013/173223). However, it was hitherto not known whether this combination of immunoregulatory antibodies would be similarly effective in other tumor types.

NSCLC is the leading cause of cancer death in the U.S. and worldwide (NCCN GUIDELINES®, Version 3.2014— Non-Small Cell Lung Cancer, available at: www.nccn.org/professionals/physician_gls/pdf/nscl.pdf, last accessed May 14, 2014). NSCLCs are relatively insensitive to chemotherapy but patients with Stage IV disease who have a good performance status (PS) benefit from treatment with chemotherapeutic drugs, including platinum agents (e.g., cisplatin, carboplatin), taxanes agents (e.g., paclitaxel, albumin-bound paclitaxel, docetaxel), vinorelbine, vinblastine, etoposide, pemetrexed and gemcitabine, and various combinations of these drugs.

SUMMARY OF THE INVENTION

The present disclosure relates to a method for treating a subject afflicted with a lung cancer comprising administering to the subject a combination of: (a) an antibody or an antigen-binding portion thereof that binds specifically to a Programmed Death-1 (PD-1) receptor and inhibits PD-1 activity, wherein the PD-1 antibody or an antigen-binding portion thereof is administered at a dose ranging from about 0.1 mg/kg to about 5.0 mg/kg body weight once about every two weeks; and (b) an antibody or an antigen-binding portion thereof that binds specifically to Cytotoxic T-Lymphocyte Antigen-4 (CTLA-4) and inhibits CTLA-4 activity, wherein the CTLA-4 antibody or an antigen-binding portion thereof is administered at a dose ranging from about 1 mg/kg to about 5.0 mg/kg body weight once about every six or twelve weeks. In certain embodiments, the lung cancer is non-small cell lung cancer (NSCLC). In other embodiments, the NSCLC has a squamous histology. In yet other embodiments, the NSCLC has a non-squamous histology.

In some embodiments, the anti-PD-1 antibody or antigen-binding portion thereof cross-competes with nivolumab for binding to human PD-1. In embodiments, the anti-PD-1 antibody or antigen-binding portion thereof is a chimeric, humanized or human monoclonal antibody or a portion thereof. In other embodiments, the anti-PD-1 antibody or antigen-binding portion thereof comprises a heavy chain constant region which is of a human IgG1 or IgG4 isotype. In certain embodiment, the anti-PD-1 antibody is nivolumab. In one embodiment, the anti-PD-1 antibody is pembrolizumab.

In certain embodiments, the anti-CTLA-4 antibody or antigen-binding portion thereof is a chimeric, humanized or human monoclonal antibody or a portion thereof. In some embodiments, the anti-CTLA-4 antibody or antigen-binding portion thereof comprises a heavy chain constant region which is of a human IgG1 isotype. In certain embodiments, the anti-CTLA-4 antibody is ipilimumab. In other embodiments, the anti-CTLA-4 antibody is tremelimumab. In some embodiments, the anti-CTLA-4 antibody or antigen-binding portion thereof cross-competes with ipilimumab for binding to human CTLA-4.

In certain embodiments, the anti-PD-1 antibody or antigen-binding portion thereof is administered at a dose of about 1 mg/kg or about 3 mg/kg body weight once about every 2 weeks. In certain embodiments, the anti-CTLA-4 antibody or antigen-binding portion thereof is administered at a dose of about 1 mg/kg body weight. In other embodiments, the anti-PD-1 antibody or antigen-binding portion thereof is administered at a dose of about 3 mg/kg body weight once about every 2 weeks and the anti-CTLA-4 antibody or antigen-binding portion thereof is administered at a dose of about 1 mg/kg body weight once about every 12 weeks. In certain embodiments, the anti-PD-1 antibody or antigen-binding portion thereof is administered at a dose of about 1 mg/kg body weight once about every 2 weeks and the anti-CTLA-4 antibody or antigen-binding portion thereof is administered at a dose of about 1 mg/kg body weight once about every 6 weeks.

In certain embodiments, a subject treated with a disclosed method exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years. In some embodiments, the subject exhibits progression-free survival of at least about eight months after the initial administration.

In certain embodiments, a subject has a longer progression-free survival when subject is treated with an anti-PD-1 antibody or antigen-binding portion thereof administered at a dose of 3 mg/kg body weight once every 2 weeks and an anti-CTLA-4 antibody or antigen-binding portion thereof administered at a dose of 1 mg/kg body weight every 12 weeks ("regimen A") than when the subject is treated with an anti-PD-1 antibody or antigen-binding portion thereof administered at a dose of 1 mg/kg body weight once every 2 weeks and an anti-CTLA-4 antibody or antigen-binding portion thereof administered at a dose of 1 mg/kg body weight every 6 weeks ("regimen B"). In some embodiments, the progression-free survival of subjects administered regimen A is at least about 1 week, at least about 2 weeks, at least about 3 weeks, at least about 1 month, at least about 2 months, at least about 3 months, at least about 4 months, at least about 5 months or at least about six months longer than the progression-free survival of subjects administered regimen B. In embodiments, the progression-free survival of subjects administered regimen A is at least about 3 months longer than the progression-free survival of subjects administered regimen B.

In certain embodiments, a subject has a longer progression-free survival when subject is treated with an anti-PD-1 antibody or antigen-binding portion thereof administered at a dose of 3 mg/kg body weight once every 2 weeks and an anti-CTLA-4 antibody or antigen-binding portion thereof administered at a dose of 1 mg/kg body weight every 12 weeks ("regimen A") than when the subject is treated with an anti-PD-1 antibody or antigen-binding portion thereof administered at a dose of 3 mg/kg body weight once every 2 weeks ("regimen C"). In embodiments, the progression-free survival of subjects administered regimen A is at least about 1 week, at least about 2 weeks, at least about 3 weeks, at least about 4 weeks, at least about 5 weeks, at least about 6 weeks, at least about 7 weeks, at least about 8 weeks, at least about 9 week, at least about 10 weeks, at least about 11 weeks, at least about 12 weeks, at least about 13 weeks, at least about 14 weeks, or at least about 15 weeks longer than the progression-free survival of subjects administered regimen C. In some embodiments, the progression-free survival of subjects administered regimen A is at least about 3 months longer than the progression-free survival of subjects administered regimen C.

In certain embodiments, the subject has a lung tumor that has ≥1% PD-L1, ≥5% PD-L1, ≥10% PD-L1, ≥25% PD-L1, or ≥50% PD-L1 expression. In certain embodiments, the combination is administered for as long as clinical benefit is observed or until disease progression or unmanageable toxicity occurs. In one embodiment, the anti-PD-1 and anti-CTLA-4 antibodies are formulated for intravenous administration. In certain embodiments, the anti PD-1 antibody or antigen-binding portion thereof and the anti-CTLA-4 antibody or antigen-binding portion thereof are administered sequentially to the subject. In some embodiments, the anti-PD-1 and anti-CTLA-4 antibodies are administered within 30 minutes of each other. In one embodiment, the anti-PD-1 antibody or antigen-binding portion thereof is administered before the anti-CTLA-4 antibody or antigen-binding portion thereof. In another embodiment, the anti-CTLA-4 antibody or antigen-binding portion thereof is administered before the anti-PD-1 antibody or antigen-binding portion thereof. In some embodiments, the anti-PD-1 antibody or antigen-binding portion thereof and the anti-CTLA-4 antibody or antigen-binding portion thereof are administered concurrently in separate compositions. In certain embodiments, the anti-PD-1 antibody or antigen-binding portion thereof and the anti-CTLA-4 antibody or antigen-binding portion thereof are administered concurrently as a single composition.

In one embodiment, the anti-PD-1 antibody or antigen-binding portion thereof is administered at a subtherapeutic dose. In certain embodiments, the anti-CTLA-4 antibody or antigen-binding portion thereof is administered at a subtherapeutic dose. In some embodiments, the anti-PD-1 antibody or antigen-binding portion thereof and the anti-CTLA-4 antibody or antigen-binding portion thereof are each administered at a subtherapeutic dose.

The present disclosure also relates to a kit for treating a subject afflicted with a lung cancer, the kit comprising: (a) an amount ranging from about 4 mg to about 500 mg of an anti-PD-1 antibody or an antigen-binding portion thereof; (b) an amount ranging from about 40 mg to about 500 mg of a CTLA-4 antibody or an antigen-binding portion thereof; and (c) instructions for using the PD-1 antibody or an antigen-binding portion thereof and the CTLA-4 antibody or an antigen-binding portion thereof in any disclosed method.

Other features and advantages of the instant invention will be apparent from the following detailed description and examples which should not be construed as limiting. The contents of all cited references, including scientific articles, newspaper reports, GenBank entries, patents and patent applications cited throughout this application are expressly incorporated herein by reference.

BRIEF DESCRIPTION OF THE DRAWINGS

FIG. 1 shows the dosing schedule for nivolumab and ipilimumab.

FIGS. 7A-7D show a case of pathological CR.

DETAILED DESCRIPTION OF THE INVENTION

Figure 2A:
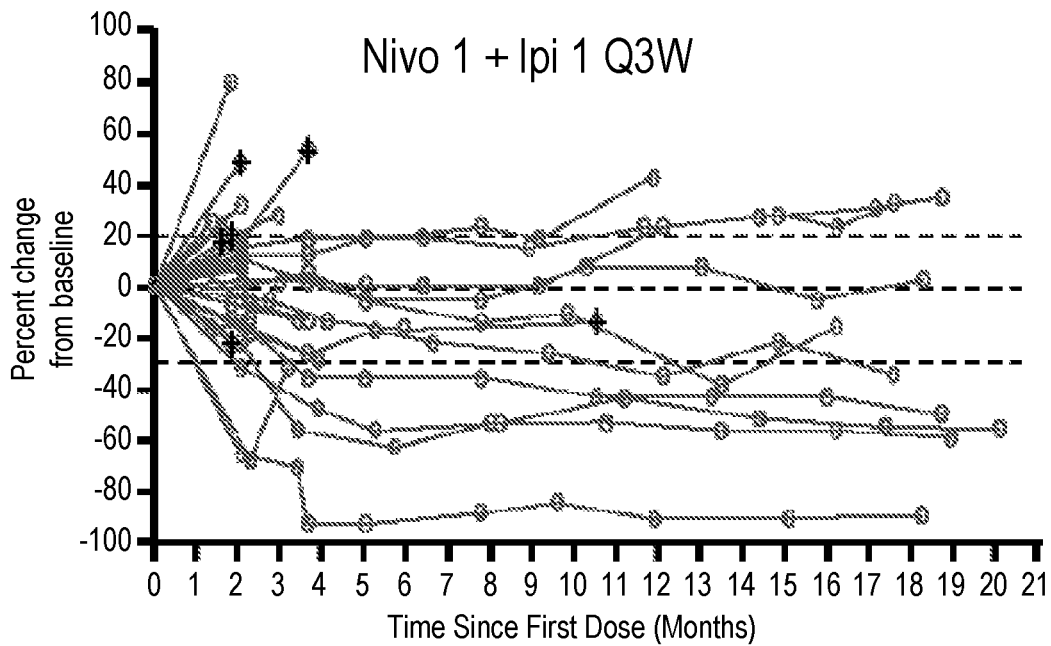
FIGS. 2A-2D show the percent change in target lesions from the baseline for treatment arms nivolumab 1 mg/kg+ipilimumab 1 mg/kg Q3 W (FIG. 2A); nivolumab 1 mg/kg Q2 W+ipilimumab 1 mg/kg Q6 W (FIG. 2B); nivolumab 3 mg/kg Q2 W+ipilimumab 1 mg/kg Q12 W (FIG. 2C); and nivolumab 3 mg/kg Q2 W+ipilimumab 1 mg/kg Q6 W (FIG. 2D).
Figure 2B:
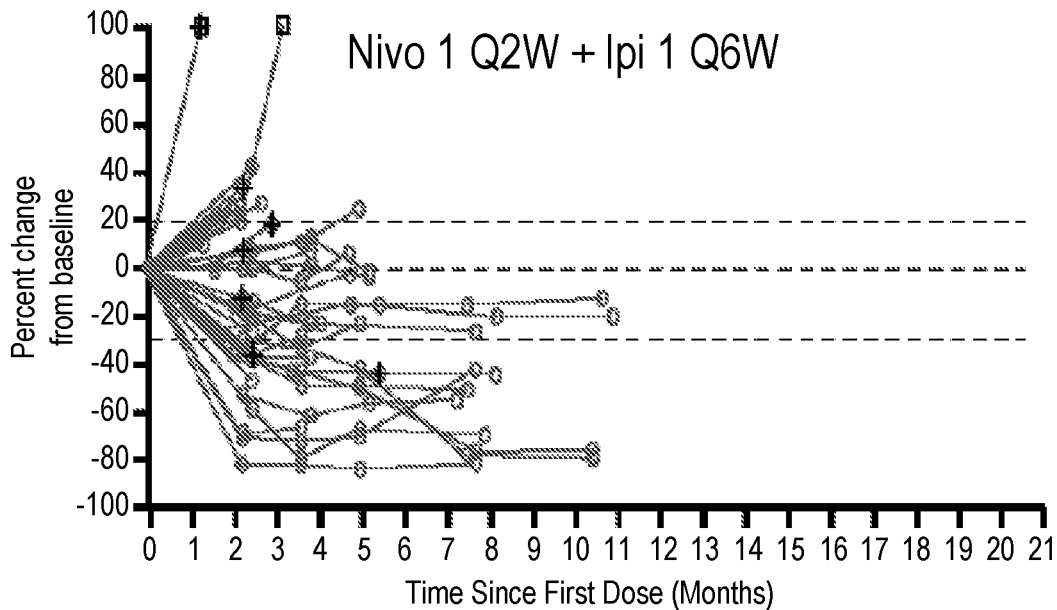
Figure 2C:
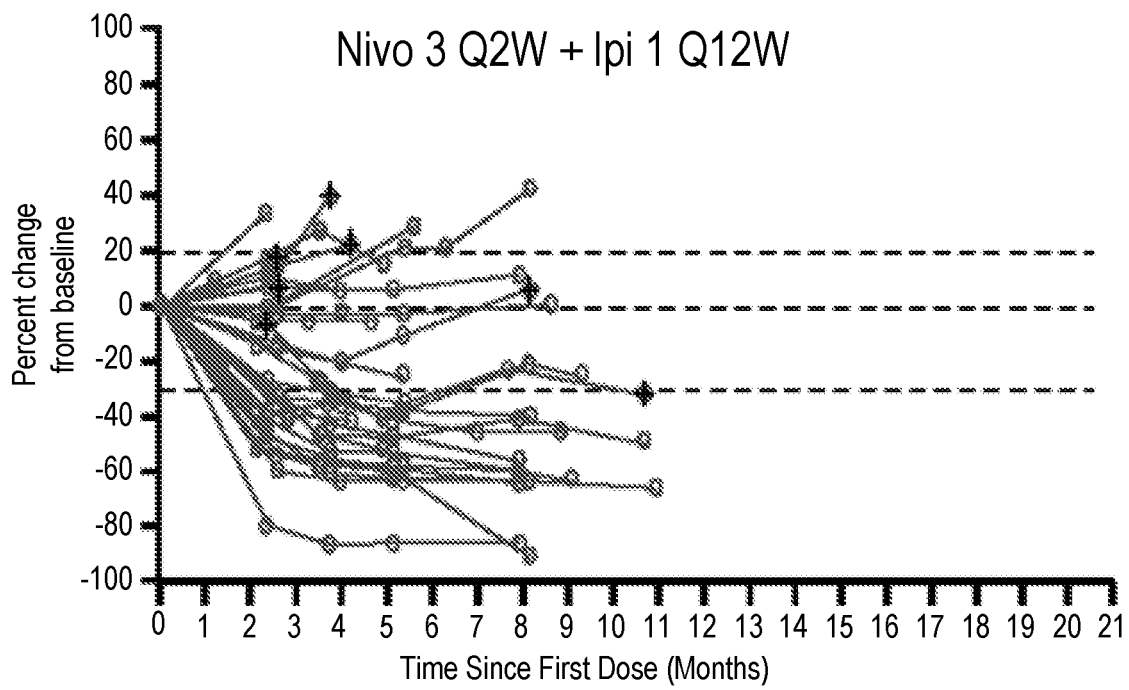
Figure 2D:
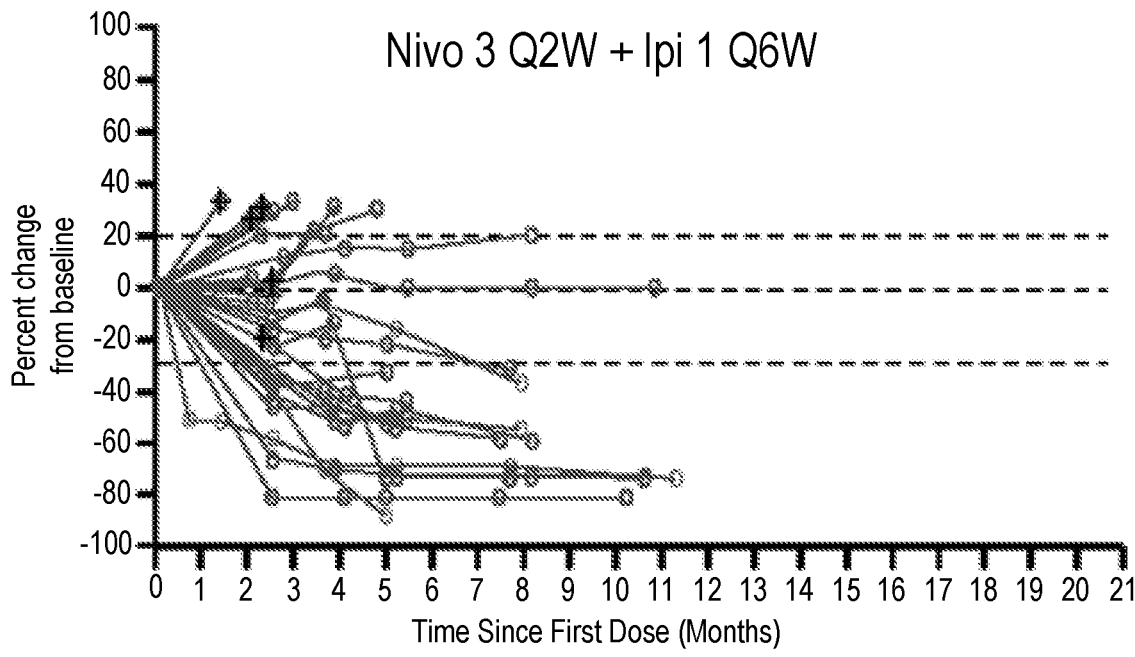

The present invention relates to methods for treating a lung cancer patient comprising administering to the patient a combination of an anti-PD-1 antibody and another anti-cancer agent. In certain embodiments, the other anti-cancer agent is an anti-CTLA-4 antibody.

Terms

In order that the present disclosure can be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the combination is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. Monoclonal antibodies can be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and can also metastasize to distant parts of the body through the lymphatic system or bloodstream.

"Cytotoxic T-Lymphocyte Antigen-4 (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"PD-L1 positive" as used herein can be interchangeably used with "PD-L1 expression of at least about 1%." In one embodiment, the PD-L1 expression can be used by any methods known in the art. In another embodiment, the PD-L1 expression is measured by an automated IHC. PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain embodiments, "PD-L1 positive" means that there are at least 100 cells that express PD-L1 on the surface of the cells.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject or prevents further tumor growth. In certain embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth or tumor growth by at least about 20%, by at least about 40%, by at least about 60%, or by at least about 80% relative to untreated subjects. In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In certain embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

The term "weight based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the invention means that two or more different antibodies in a single composition (e.g., anti-PD-1 antibody and a second antibody, e.g., anti-CTLA-4 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CTLA-4 antibody). For example, the 3:1 ratio of an anti-PD-1 antibody and an anti-CTLA-4 antibody can mean that a vial can contain about 240 mg of the anti-PD-1 antibody and 80 mg of the anti-CTLA-4 antibody or about 3 mg/ml of the anti-PD-1 antibody and 1 mg/ml of the anti-CTLA-4 antibody.

The use of the term "flat dose" with regard to the methods and dosages of the invention means a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of an antibody (e.g., 240 mg of an anti-PD-1 antibody).

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Methods of the Invention

This disclosure provides a method of treating a subject afflicted with a lung cancer, which method comprises administering to the subject a combination of therapeutically effective amounts of: (a) an anti-cancer agent which is an antibody or an antigen-binding portion thereof that specifically binds to and a PD-1 receptor and inhibits PD-1 activity; and (b) an anti-CTLA-4 antibody. As NSCLC comprises more than 85% of lung tumors, in embodiments the lung cancer is NSCLC. In other embodiments, the subject is a human patient. In certain embodiments, the subject is a chemotherapy-naïve patient (e.g., a patient who has not previously received any chemotherapy). In other embodiments, the subject for the present combination therapy has received another cancer therapy (e.g., a chemotherapy), but is resistant or refractory to such another cancer therapy. In certain specific embodiments, the subject for the present combination therapy has cancer cells expressing mutated forms of the EGFR or KRAS gene. In certain embodiments, the subject has cancer cells that are PD-L1+. In certain embodiments, the subject has cancer cells that are PD-L1−. In some embodiments, the subject never smoked. In certain embodiments, the subject formerly smoked. In one embodiment, the subject currently smokes. In certain embodiments, the subject has cancer cells that are squamous. In certain embodiments, the subject has cancer cells that are non-squamous.

In certain embodiments, the therapy of the present invention (e.g., administration of an anti-PD-1 antibody and a CTLA-4 antibody) effectively increases the duration of survival of the subject. In some embodiments, the anti-PD-1 antibody combination therapy of the present invention increases the progression-free survival of the subject. In certain embodiments, the anti-PD-1 antibody combination therapy of the present invention increases the progression-free survival of the subject in comparison to standard-of-care therapies. In some embodiments, the anti-PD-1 antibody combination therapy of the present invention increases the progression-free survival of the subject in comparison to an anti-PD-1 antibody alone. In some embodiments, the anti-PD-1 antibody combination therapy of the present invention increases the progression-free survival of the subject in comparison to other anti-PD-1 antibody combinations. After the administration of an anti-PD-1 antibody combination therapy, the subject having a lung cancer tumor can exhibit an overall survival of at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the administration.

In other embodiments, the duration of survival or the overall survival of the subject is increased by at least about 1 month, at least about 2 months, at least about 3 months, at least about 4 months, at least about 6 months, or at least about 1 year when compared to another subject treated with only a standard-of-care therapy (e.g., docetaxel), an anti-PD-1 antibody alone, or a different dosing schedule of the combination therapy. For example, the duration of survival or the overall survival of the subject treated with an anti-PD-1 antibody combination disclosed herein is increased by at least about 5%, at least about 10%, at least about 15%, at least about 20%, at least about 25%, at least about 30%, at least about 40%, at least about 50% or at least about 75% when compared to another subject treated with only a standard-of-care therapy (e.g., docetaxel), an anti-PD-1 antibody alone or a different dosing schedule of the combination therapy.

In certain embodiments, the therapy of the present invention effectively increases the duration of progression free survival of the subject. In some embodiments, the subject exhibits a progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years.

In some embodiments, the subject has a longer progression-free survival when the anti-PD-1 antibody or antigen-binding portion thereof is administered at a dose of 3 mg/kg body weight once every 2 weeks and the anti-CTLA-4 antibody or antigen-binding portion thereof is administered at a dose of 1 mg/kg body weight every 6 to 12 weeks (e.g., every 6 or 12 weeks) than when the subject is treated with an anti-PD-1 antibody or antigen-binding portion thereof administered at a dose of 3 mg/kg body weight once every 2 weeks. In some embodiments, the progression-free survival of the subject treated with the anti-PD-1 antibody or antigen-binding portion thereof at a dose of 3 mg/kg body weight once every 2 weeks and the anti-CTLA-4 antibody or antigen-binding portion thereof at a dose of 1 mg/kg body weight every 6 or 12 weeks is at least about 1 week is at least about 2 weeks, at least about 3 weeks, at least about 1 month, at least about 2 months, at least about 3 months, at least about 4 months, at least about 5 months, at least about six months, at least about 7 months, at least about 8 months, at least about 9 months, at least about 10 months, at least about 11 months, or at least about 1 year longer than when the subject is treated with an anti-PD-1 antibody or antigen-binding portion thereof administered at a dose of 3 mg/kg body weight once every 2 weeks. In some embodiments, the progression-free survival of the subject is at least about 3 months longer when the anti-PD-1 antibody or antigen-binding portion thereof is administered at a dose of 3 mg/kg body weight once every 2 weeks and the anti-CTLA-4 antibody or antigen-binding portion thereof is administered at a dose of 1 mg/kg body weight every 6 or 12 weeks than when the subject is treated with an anti-PD-1 antibody or antigen-binding portion thereof administered at a dose of 3 mg/kg body weight once every 2 weeks. In some embodiments, the anti-CTLA-4 antibody or antigen-binding portion thereof is administered every six weeks. In other embodiments, the anti-CTLA-4 antibody or antigen-binding portion thereof is administered every twelve weeks.

In some embodiments, the subject has a longer progression-free survival when the anti-PD-1 antibody or antigen-binding portion thereof is administered at a dose of 3 mg/kg body weight once every 2 weeks and the anti-CTLA-4 antibody or antigen-binding portion thereof is administered at a dose of 1 mg/kg body weight every 6 or 12 weeks than when the subject is treated with an anti-PD-1 antibody or antigen-binding portion thereof administered at a dose of 1 mg/kg body weight once every 2 weeks and an anti-CTLA-4 antibody or antigen-binding portion thereof administered at a dose of 1 mg/kg body weight every 6 weeks. In certain embodiments, the progression-free survival of the subject treated with the anti-PD-1 antibody or antigen-binding portion thereof at a dose of 3 mg/kg body weight once every 2 weeks and the anti-CTLA-4 antibody or antigen-binding portion thereof at a dose of 1 mg/kg body weight every 6 or 12 weeks is at least about 1 week, at least about 2 weeks, at least about 3 weeks, at least about 1 month, at least about 2 months, at least about 3 months, at least about 4 months, at least about 5 months or at least about six months longer than when the subject is treated with an anti-PD-1 antibody or antigen-binding portion thereof administered at a dose of 1 mg/kg body weight once every 2 weeks and an anti-CTLA-4 antibody or antigen-binding portion thereof administered at a dose of 1 mg/kg body weight every 6 weeks. In some embodiments, the progression-free survival is at least about 3 months longer when the anti-PD-1 antibody or antigen-binding portion thereof is administered at a dose of 3 mg/kg body weight once every 2 weeks and the anti-CTLA-4 antibody or antigen-binding portion thereof is administered at a dose of 1 mg/kg body weight every 6 or 12 weeks than when the subject is treated with an anti-PD-1 antibody or antigen-binding portion thereof administered at a dose of 1 mg/kg body weight once every 2 weeks and an anti-CTLA-4 antibody or antigen-binding portion thereof administered at a dose of 1 mg/kg body weight every 6 weeks or when the subject is treated with a standard of care therapy. In some embodiments, the anti-CTLA-4 antibody or antigen-binding portion thereof is administered every six weeks. In other embodiments, the anti-CTLA-4 antibody or antigen-binding portion thereof is administered every twelve weeks.

The PD-L1 status of a tumor in a subject can be measured prior to administering any composition or utilizing any method disclosed herein. In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of the subject is at least about 5%. In a certain embodiment, the PD-L1 status of a tumor is at least about 10%. In a one embodiment, the PD-L1 status of the tumor is at least about 25%. In a particular embodiment, the PD-L1 status of the tumor is at least about 50%.

In some embodiments, the median progression-free survival of a subject with a tumor that has ≥1% PD-L1 expression is at least about 1 week, at least about 2 weeks, at least about 3 weeks, at least about 4 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year longer than the median progression-free survival of a subject with a tumor with a <1% PD-L1 expression. In some embodiments, the progression-free survival of a subject with a tumor that has ≥1% PD-L1 expression is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 1 year, at least about eighteen months, at least about 2 years, at least about 3 years, at least about 4 years, or at least about 5 years.

In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12): a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.*

23(4):243-9 (2010)). In certain embodiments of any of the present methods, PD-L1 expression is assayed by immuno-PET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 mAb to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a mAb that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^+$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

$$\text{Histoscore} = [(\% \text{ tumor} \times 1(\text{low intensity})) + (\% \text{ tumor} \times 2(\text{medium intensity})) + (\% \text{ tumor} \times 3(\text{high intensity}))]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4(127):127ra37 (2012)).

The present methods can treat a non-squamous NSCLC of any stages. There are at least seven stages used for NSCLC: occult (hidden) stage, Stage 0 (carcinoma in situ), Stage I, Stage II, Stage IIIA, Stage IIIB, and Stage IV. In the occult stage, the cancer cannot be seen by imaging or bronchoscopy. In Stage 0, cancer cells are found in the lining of the airways.

In one embodiment, the present methods treat a Stage I non-squamous NSCLC. Stage I NSCLC is divided in Stage IA and IB. In Stage IA, the tumor is in the lung only and is 3 centimeters or smaller. In Stage IB, the cancer has not spread to the lymph nodes and one or more of the following is true: 1) the tumor is larger than 3 centimeters but not larger than 5 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus.

In another embodiment, the methods of the present invention treat a Stage II non-squamous NSCLC. Stage II NSCLC is divided into Stage IIA and IIB. In Stage IIA, the cancer has either spread to the lymph nodes or not. If the cancer has spread to the lymph nodes, then the cancer can only have spread to the lymph nodes on the same side of the chest as the tumor, the lymph nodes with cancer or within the lung or near the bronchus. and one or more of the following is true: 1) the tumor is not larger than 5 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. The tumor is also considered Stage IIA if the cancer has not spread to the lymph nodes and one or more of the following is true: 1) the tumor is larger than 5 centimeters but not larger than 7 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. In stage IIB, the cancer has either spread to the lymph nodes or not. If the cancer has spread to the lymph nodes, then the cancer can only have spread to the lymph nodes on the same side of the chest as the tumor, the lymph nodes with cancer are within the lung or near the bronchus and one or more of the following is true: 1) the tumor is larger than 5 centimeters but not larger than 7 centimeters; 2) the cancer has spread to the main bronchus and is at least 2 centimeters below where the trachea joins the bronchus; 3) cancer has spread to the innermost layer of the membrane that covers the lung; or 4) part of the lung has collapsed or developed pneumonitis (inflammation of the lung) in the area where the trachea joins the bronchus. The tumor is also considered Stage IIB if the cancer has not spread to the lymph nodes and one or more of the following is true: 1) the tumor is larger than 7 centimeters; 2) the cancer has spread to the main bronchus (and is at least 2 centimeters below where the trachea joins the bronchus), the chest wall, the diaphragm, or the nerve that controls the diaphragm; 3) cancer has spread to the membrane around the heart or lining the chest wall; 4) the whole lung has collapsed or developed pneumonitis (inflammation of the lung); or 5) there are one or more separate tumors in the same lobe of the lung.

In other embodiments, any methods of the present invention treats Stage III non-squamous NSCLC. Stage IIIA is divided into 3 sections. These 3 sections are based on 1) the size of the tumor; 2) where the tumor is found and 3) which (if any) lymph nodes have cancer. In the first type of Stage IIIA NSCLC, the cancer has spread to the lymph nodes on the same side of the chest as the tumor, and the lymph nodes with the cancer are near the sternum or where the bronchus enters the lung. Additionally: 1) the tumor may be any size; 2) part of the lung (where the trachea joins the bronchus) or the whole lung may have collapsed or developed pneumonitis (inflammation of the lung); 3) there may be one or more separate tumors in the same lobe of the lung; and 4) cancer can have spread to any of the following: a) main bronchus, but not the area where the trachea joins the bronchus, b) chest well, c) diaphragm and the nerve that controls it, d) membrane around the lung or lining the chest wall, e) membrane around the heart. In the second type of Stage IIIA NSCLC, the cancer has spread to the lymph nodes on the same side of the chest as the tumor, and the lymph nodes with the cancer are within the lung or near the bronchus. Additionally: 1) the tumor may be any size; 2) the whole lung may have collapsed or developed pneumonitis (inflammation of the lung); 3) there may be one or more separate tumors in the any of the lobes of the lung with cancer; and 4) cancer can have spread to any of the following: a) main bronchus, but not the area where the trachea joins the bronchus, b) chest well, c) diaphragm and the nerve that controls it, d) membrane around the lung or lining the chest wall, e) heart or the membrane around it, f) major blood vessels that lead to or from the heart, g) trachea, h) esophagus, i) nerve that controls the larynx (voice box), j) sternum (chest bone) or backbone, or k) carina (where the trachea joins the bronchi). In the third type of Stage IIIA NSCLC, the cancer has not spread to the lymph nodes, the tumor may be any size, and cancer has spread to any one of the following: a) heart, b) major blood vessels that lead to or from the heart, c) trachea, d) esophagus, e) nerve that controls the larynx (voice box), f) sternum (chest bone) or backbone, or g) carina (where the trachea joins the bronchi). Stage IIIB is divided into 2 sections depending on 1) the size of the tumor, 2) where the tumor is found, and 3) which lymph nodes have cancer. In the first type of Stage IIIB NSCLC, the cancer has spread to the lymph nodes on the opposite side of the chest as the tumor. Additionally, 1) the tumor may be any size; 2) part of the lung (where the trachea joins the bronchus) or the whole lung may have collapsed or developed pneumonitis (inflammation of the lung); 3) there may be one or more separate tumors in any of the lobes of the lung with cancer; and 4) cancer may have spread to any of the following: a) main bronchus, b) chest well, c) diaphragm and the nerve that controls it, d) membrane around the lung or lining the chest wall, e) heart or the membrane around it, f) major blood vessels that lead to or from the heart, g) trachea, h) esophagus, i) nerve that controls the larynx (voice box), j) sternum (chest bone) or backbone, or k) carina (where the trachea joins the bronchi). In the second type of Stage IIIB NSCLC, the cancer has spread to lymph nodes on the same side of the chest as the tumor. The lymph nodes with cancer are near the sternum (chest bone) or where the bronchus enters the lung. Additionally, 1) the tumor may be any size; 2) there may be separate tumors in different lobes of the same lung; and 3) cancer has spread to any of the following: a) heart, b) major blood vessels that lead to or from the heart, c) trachea, d) esophagus, e) nerve that controls the larynx (voice box), f) sternum (chest bone) or backbone, or g) carina (where the trachea joins the bronchi).

In some embodiments, the methods of the invention treat a Stage IV non-squamous NSCLC. In Stage IV NSCLC, the tumor may be any size and the cancer may have spread to the lymph nodes. One or more of the following is true in Stage IV NSCLC: 1) there are one or more tumors in both lungs; 2) cancer is found in the fluid around the lungs or heart; and 3) cancer has spread to other parts of the body, such as the brain, liver, adrenal glands, kidneys or bone.

This disclosure provides combination therapy methods for treating lung cancer wherein an anti-PD-1 antibody is combined with another anti-cancer agent that is an antibody or an antigen-binding portion thereof that binds specifically to CTLA-4 and inhibits CTLA-4 activity. The combination of the anti-PD-1 antibody, nivolumab, and the anti-CTLA-4 antibody, ipilimumab, has been demonstrated herein (see Example 1) to produce early, durable antitumor activity in NSCLC patients, particularly with specific dosing schedules. Accordingly, in certain embodiments, the anti-CTLA-4 antibody that is used in combination with the anti-PD-1 antibody is ipilimumab. In embodiments, the anti-CTLA-4 antibody is tremelimumab. In other embodiments, the anti-CTLA-4 antibody or antigen-binding portion thereof is an antibody or portion thereof that cross-competes with ipilimumab for binding to human CTLA-4. In certain other embodiments, the anti-CTLA-4 antibody or antigen-binding portion thereof is a chimeric, humanized or human mAb or a portion thereof. In yet other embodiments, the anti-CTLA-4 antibody or antigen-binding portion thereof comprises a heavy chain constant region that is of a human IgG1 or IgG4 isotype. In some embodiments, the anti-CTLA-4 antibody comprises a heavy chain constant region that is of a human IgG1 isotype.

Because of durability of the clinical effect previously demonstrated with immunotherapy by inhibition of immune checkpoints (see, e.g., WO 2013/173223), the combination treatment can include, in alternative embodiments, a finite number of doses, e.g., about 1-10 doses, or can involve dosing at long intervals, e.g., once about every 3-6 months or once about every 1-2 years or longer intervals.

In certain embodiments of the present methods, the anti-PD-1 antibody is nivolumab. In other embodiments, it is pembrolizumab. In yet other embodiments, the anti-CTLA-4 antibody is ipilimumab. In further embodiments, the anti-CTLA-4 antibody is tremelimumab. Typically, the anti-PD-1 and anti-CTLA-4 antibodies are formulated for intravenous administration. In certain embodiments, when the anti-PD-1 and anti-CTLA-4 antibodies are administered in combination, they are administered within 30 minutes of each other. Either antibody can be administered first, that is, in certain embodiments, the anti-PD-1 antibody is administered before the anti-CTLA-4 antibody, whereas in other embodiments, the anti-CTLA-4 antibody is administered before the anti-PD-1 antibody. Typically, each antibody is administered by intravenous infusion over a period of 60 minutes. In certain embodiments, the anti-PD-1 and anti-CTLA-4 antibodies are administered concurrently, either admixed as a single composition in a pharmaceutically acceptable formulation for concurrent administration, or concurrently as separate compositions with each antibody in a pharmaceutically acceptable formulation.

In certain embodiments, the anti-PD-1 antibody or antigen-binding portion thereof is administered at a subtherapeutic dose. In certain other embodiments, the anti-CTLA-4 antibody or antigen-binding portion thereof is administered at a subtherapeutic dose. In further embodiments, both the anti-PD-1 antibody or antigen-binding portion thereof and the anti-CTLA-4 antibody or antigen-binding portion thereof are each administered at a subtherapeutic dose.

Anti-PD-1 Antibodies or Anti-PD-L1 Antibodies Useful for the Invention

HuMAbs that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present invention include monoclonal antibodies that bind specifically to human PD-1 and exhibit at least one, in some embodiments, at least five, of the preceding characteristics. In some embodiments, the anti-PD-1 antibody is nivolumab. In one embodiment, the anti-PD-1 antibody is pembrolizumab.

In certain embodiments, the anti-PD-1 antibody or antigen-binding portion thereof cross-competes with nivolumab for binding to human PD-1. In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody or fragment thereof cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody or fragment thereof cross-competes with MEDI0608. In still other embodiments, the anti-PD-1 antibody or fragment thereof binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089B2.

In certain embodiments, an immune checkpoint inhibitor is AMP-224, which is a B7-DC Fc fusion protein. AMP-224 is discussed in U.S. Publ. No. 2013/0017199 or in www.cancer.gov/publications/dictionaries/cancer-drug?cdrid=700595 (last accessed Jul. 8, 2015).

In other embodiments, the anti-PD-1 antibody or fragment thereof cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies usable in the disclosed methods also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab are monoclonal antibodies. For administration to human subjects, these cross-competing antibodies are chimeric antibodies, or humanized or human antibodies. Such chimeric, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies suitable for use in the disclosed methods or compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region that is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014 Cancer Immunol Res. 2(9):846-56). In yet other embodiments, the antibody comprises a light chain constant region that is a human kappa or lambda constant region. In other embodiments, the anti-PD-1 antibody or antigen-binding portion thereof is a mAb or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or BGB-A317.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

In certain embodiments, an anti-PD-1 antibody used in the methods can be replaced with another PD-1 or anti-PD-L1 antagonist. For example, because an anti-PD-L1 antibody prevents interaction between PD-1 and PD-L1, thereby exerting similar effects to the signaling pathway of PD-1, an anti-PD-L1 antibody can replace the use of an anti-PD-1 antibody in the methods disclosed herein. Therefore, in one embodiment, the present invention is directed to a method for treating a subject afflicted with a NSCLC comprising administering to the subject a therapeutically effective amount an anti-PD-L1 antibody and an anti-CTLA-4 antibody.

In certain embodiments, the anti-PD-L1 antibody useful for the method is BMS-936559 (formerly 12A4 or MDX-1105) (see, e.g., U.S. Pat. No. 7,943,743; WO 2013/173223).

In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149).

In other embodiments, the anti-PD-L1 antibody is MEDI4736 (also called Durvalumab; Khleif (2013) In: Proceedings from the European Cancer Congress 2013; Sep. 27-Oct. 1, 2013; Amsterdam, The Netherlands. Abstract 802, See U.S. Pat. No. 8,779,108 or US 2014/0356353, filed May 6, 2014).

In further embodiments, the anti-PD-L1 antibody is MSB0010718C (also called Avelumab; See US 2014/0341917)

Because anti-PD-1 and anti-PD-L1 antibodies target the same signaling pathway and have been shown in clinical trials to exhibit similar levels of efficacy in a variety of cancers, including RCC (see Brahmer et al. (2012) *N Engl J Med* 366:2455-65; Topalian et al. (2012a) *N Engl J Med* 366:2443-54; WO 2013/173223), an anti-PD-L1 antibody can be substituted for the anti-PD-1 antibody in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149) or MEDI4736 (Khleif (2013) In: Proceedings from the European Cancer Congress 2013; Sep. 27-Oct. 1, 2013; Amsterdam, The Netherlands. Abstract 802). In certain embodiments, the antibodies that cross-compete for binding to human PD-L1 with, or bind to the same epitope region of human PD-L1 as the above-references PD-L1 antibodies are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art.

In some embodiments, an immune checkpoint inhibitor, e.g., an anti-PD-1 antagonist, used in the present invention is a PD-1 Fc fusion protein.

The anti-PD-1 antibody or antigen binding portion thereof or the anti-PD-L1 antibody antigen binding portion thereof of the present invention can be administered to a subject at a dose (either a first dose or a second dose) selected from the group consisting of about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.5 mg/kg, about 6.5 mg/kg, about 7.5 mg/kg, about 8.0 mg/kg, about 8.5 mg/kg, about 9.0 mg/kg, about 9.5 mg/kg, about 10 mg/kg, about 11 mg/kg, about 12 mg/kg, about 13 mg/kg, about 14 mg/kg, about 15 mg/kg, about 20 mg/kg, or greater than about 20 mg/kg. In other embodiments, the anti-PD-1 antibody or antigen binding portion thereof or the anti-PD-L1 antibody or antigen binding portion thereof, can be administered at a dose selected from the group consisting of about 0.1 to about 20.0 mg/kg, about 0.1 to about 15.0 mg/kg, about 0.1 to about 10.0 mg/kg, about 0.1 to about 9.5 mg/kg, about 0.1 to about 9.0 mg/kg, about 0.1 to about 8.5 mg/kg, about 0.1 to about 8.0 mg/kg, about 0.1 to about 7.5 mg/kg, about 0.1 to about 7.0 mg/kg, about 0.1 to about 6.5 mg/kg, about 0.1 to about 6.0 mg/kg, about 0.1 to about 5.5 mg/kg, about 0.1 to about 5.0 mg/kg, about 0.1 to about 4.5 mg/kg, about 0.1 to about 4.0 mg/kg, about 0.1 to about 3.5 mg/kg, about 0.1 to about 3.0 mg/kg, about 0.3 to about 10.0 mg/kg, about 0.3 to about 9.0 mg/kg, about 0.3 to about 6.0 mg/kg, about 0.3 to about 3.0 mg/kg, about 3.0 to about 10.0 mg/kg, about 3.0 to about 9.0 mg/kg, or about 3.0 to about 6.0 mg/kg. In certain embodiments, a subject is administered 0.3 mg/kg of an anti-PD-1 antibody, e.g., nivolumab, or an anti-PD-L1 antibody. In other embodiments, a subject is administered 2.0 mg/kg of an anti-PD-1 antibody, e.g., nivolumab, or an anti-PD-L1 antibody. In other embodiments, a subject is administered 10 mg/kg of an anti-PD-1 antibody, e.g., nivolumab, or an anti-PD-L1 antibody.

Anti-CTLA-4 Antibodies Useful for the Invention

Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

HuMAbs that bind specifically to CTLA-4 with high affinity have been disclosed in U.S. Pat. Nos. 6,984,720 and 7,605,238. Other anti-CTLA-4 monoclonal antibodies have been described in, for example, U.S. Pat. Nos. 5,977,318, 6,051,227, 6,682,736, and 7,034,121. The anti-CTLA-4 HuMAbs disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$, and (d) inhibits the binding of CTLA-4 to B7-1 (CD80) and B7-2 (CD86). Anti-CTLA-4 antibodies usable in the present invention include monoclonal antibodies that bind specifically to human CTLA-4 and exhibit at least one, at least two or, in one embodiment, at least three of the preceding characteristics. An exemplary clinical anti-CTLA-4 antibody is the human mAb 10D1 (now known as ipilimumab and marketed as YERVOY®) as disclosed in U.S. Pat. No. 6,984,720. Ipilimumab is an anti-CTLA-4 antibody for use in the methods disclosed herein. Another anti-CTLA-4 antibody usable in the present methods is tremelimumab.

An exemplary clinical anti-CTLA-4 antibody is the human mAb 10D1 (now known as ipilimumab and marketed as YERVOY®) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies usable in the disclosed methods also include isolated antibodies that bind specifically to human PD-1 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human PD-1 as does ipilimumab or tremelimumab, are antibodies comprising a heavy chain of the human IgG1 isotype. For administration to human subjects, these cross-competing antibodies are chimeric antibodies, or humanized or human antibodies. Usable anti-CTLA-4 antibodies also include antigen-binding portions of the above antibodies such as Fab, F(ab")2, Fd or Fv fragments.

Ipilimumab (YERVOY®) is a fully human, IgG1 monoclonal antibody that blocks the binding of CTLA-4 to its B7 ligands, thereby stimulating T cell activation and improving overall survival (OS) in patients with advanced melanoma (Hodi et al. (2010) *N Engl J Med* 363:711-23). Concurrent therapy with nivolumab and ipilimumab in a Phase 1 clinical trial produced rapid and deep tumor regression in a substantial proportion of patients with advanced melanoma, and was significantly more effective than either antibody alone (Wolchok et al. (2013) *N Engl J Med* 369(2):122-33; WO 2013/173223). However, it was hitherto not known whether this combination of immunoregulatory antibodies would be similarly effective in other tumor types.

Standard-of-Care Therapies for Lung Cancer

Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES® (2014), available at: www.nccn.org/professionals/physician_gls/f_guidelines asp, last accessed May 14, 2014).

NSCLC is the leading cause of cancer death in the U.S. and worldwide, exceeding breast, colon and prostate cancer combined. In the U.S., an estimated 228,190 new cases of lung and bronchial will be diagnosed in the U.S., and some 159,480 deaths will occur because of the disease (Siegel et al. (2014) *CA Cancer J Clin* 64(1):9-29). The majority of patients (approximately 78%) are diagnosed with advanced/recurrent or metastatic disease. Metastases to the adrenal gland from lung cancer are a common occurrence, with about 33% of patients having such metastases. NSCLC therapies have incrementally improved OS, but benefit has reached a plateau (median OS for late stage patients is just 1 year). Progression after 1 L therapy occurred in nearly all of these subjects and the 5-year survival rate is only 3.6% in the refractory setting. From 2005 to 2009, the overall 5-year relative survival rate for lung cancer in the U.S. was 15.9% (NCCN GUIDELINES®, Version 3.2014-Non-Small Cell Lung Cancer, available at: www.nccn.org/professionals/physician_gls/pdf/nscl.pdf, last accessed May 14, 2014).

Surgery, radiation therapy (RT) and chemotherapy are the three modalities commonly used to treat NSCLC patients. As a class, NSCLCs are relatively insensitive to chemotherapy and RT, compared to small cell carcinoma. In general, for patients with Stage I or II disease, surgical resection provides the best chance for cure, with chemotherapy increasingly being used both pre-operatively and post-operatively. RT can also be used as adjuvant therapy for patients with resectable NSCLC, the primary local treatment, or as palliative therapy for patients with incurable NSCLC.

Patients with Stage IV disease who have a good performance status (PS) benefit from chemotherapy. Many drugs, including platinum agents (e.g., cisplatin, carboplatin), taxanes agents (e.g., paclitaxel, albumin-bound paclitaxel, docetaxel), vinorelbine, vinblastine, etoposide, pemetrexed and gemcitabine are useful for Stage IV NSCLC. Combinations using many of these drugs produce 1-year survival rates of 30% to 40% and are superior to single agents. Specific targeted therapies have also been developed for the treatment of advanced lung cancer. For example, bevacizumab (AVASTIN®) is a mAb that blocks vascular endothelial growth factor A (VEGF-A). Erlotinib (TARCEVA®) is a small-molecule TKI of epidermal growth factor receptor (EGFR). Crizotinib (XALKORI®) is a small-molecule TKI that targets ALK and MET, and is used to treat NSCLC in patients carrying the mutated ALK fusion gene. Cetuximab (ERBITUX®) is a mAb that targets EGFR.

There is a particular unmet need among patients who have squamous cell NSCLC (representing up to 25% of all NSCLC) as there are few treatment options after first line (1L) therapy. Single-agent chemotherapy is standard of care following progression with platinum-based doublet chemotherapy (Pt-doublet), resulting in median OS of approximately 7 months. Docetaxel remains the benchmark treatment in this line of therapy although erlotinib can also be used with less frequency. Pemetrexed has also been shown to produce clinically equivalent efficacy outcomes but with significantly fewer side effects compared with docetaxel in the second line (2L) treatment of patients with advanced NSCLC (Hanna et al. (2004) *J Clin Oncol* 22:1589-97). No therapy is currently approved for use in lung cancer beyond the third line (3L) setting. Pemetrexed and bevacizumab are not approved in squamous NSCLC, and molecularly targeted therapies have limited application. The unmet need in advanced lung cancer has been compounded by the recent failure of Oncothyreon and Merck KgaA's STIMUVAX® to improve OS in a phase 3 trial, inability of ArQule's and Daiichi Sankyo's c-Met kinase inhibitor, tivantinib, to meet survival endpoints, failure of Eli Lilly's ALIMTA® in combination with Roche's AVASTIN® to improve OS in a late-stage study, and Amgen's and Takeda Pharmaceutical's failure to meet clinical endpoints with the small-molecule VEGF-R antagonist, motesanib, in late-stage trials.

Immunotherapy of Lung Cancer

A clear need exists for effective agents for patients who have progressed on multiple lines of targeted therapy, as well as for therapies that extend survival for longer periods beyond the current standard treatments. Newer approaches involving immunotherapy, especially blockade of immune checkpoints including the CTLA-4, PD-1, and PD-L1 inhibitory pathways, have recently shown promise (Creelan et al. (2014) *Cancer Control* 21(1):80-89). Thus, ipilimumab in combination with chemotherapy has exhibited encouraging results in small-cell and non-small-cell lung cancer alike. In addition, dual checkpoint blockade strategies, such as those combining anti-PD-1 and anti-CTLA-4 have proven to be highly effective in treating melanoma (Wolchok et al. (2013) *N Engl J Med* 369(2): 122-33; WO 2013/173223), and other combinations including anti-PD-L1, anti-LAG-3, or anti-KIR, are being tested to increase the proportion and durability of tumor responses. By analogy to melanoma, NSCLC patients can to benefit either from the combination of different immunotherapeutic drugs or the combination of such drugs with targeted agents or other treatments including, surgery, radiation, standard cancer chemotherapies, or vaccines. Although the combination of nivolumab and ipilimumab has proven to be very efficacious in treating melanoma with manageable toxicity (Wolchok et al. (2013) *N Engl J Med* 369(2):122-33), it was not hitherto known whether this combination would be significantly more effective in human subjects than treatment of NSCLC and other cancers with the individual agents.

Pharmaceutical Compositions and Dosages

Therapeutic agents of the present invention can be constituted in a composition, e.g., a pharmaceutical composition containing one or more antibodies and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion). A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

The present disclosure provides dosage regimens that can provide a desired response, e.g., a maximal therapeutic response and/or minimal adverse effects. For administration of an anti-PD-1 antibody, especially in combination with an anti-CTLA-4 antibody, the dosage can range from about 0.01 to about 20 mg/kg, about 0.1 to about 10 mg/kg, about 0.01 to about 5 mg/kg, about 1 to about 5 mg/kg, about 2 to about 5 mg/kg, about 1 to about 3 mg/kg, about 7.5 to about 12.5 mg/kg, or about 0.1 to about 30 mg/kg of the subject's body weight. For example, dosages can be about 0.1, about 0.3, about 1, about 2, about 3, about 4, about 5, or about 10 mg/kg body weight. The dosing schedule is typically designed to achieve exposures that result in sustained receptor occupancy (RO) based on typical pharmacokinetic properties of an antibody. An exemplary treatment regime entails administration once about per week, once about every 2 weeks, once about every 3 weeks, once about every 4 weeks, once about every month, once about every 3-6 months or longer. In certain embodiments, an anti-PD-1 antibody such as nivolumab is administered to the subject once about every 2 weeks. The anti-PD-1 antibody can be administered in at least two doses, each of the doses is at an amount of about 0.01 mg/kg to about 5 mg/kg, e.g., 3 mg/kg, at a dosing interval of every two weeks between the two doses. In some embodiments, the anti-PD-1 antibody is administered in at least three, four, five, six, or seven doses (i.e., multiple doses), each of the doses is at an amount of about 0.01 mg/kg to about 5 mg/kg, e.g., 3 mg/kg, at a dosing interval of every two weeks between two adjacently given doses. The dosage and scheduling can change during a course of treatment. In one embodiment, a dosage regimen for an anti-PD-1 antibody of the invention comprises about 0.3-1 about 5 mg/kg body weight, 1-5 mg/kg body weight, or about 1-about 3 mg/kg body weight via intravenous administration, with the antibody being given every about 14-21 days in up to about 6-week or about 12-week cycles until complete response or confirmed progressive disease. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

When used in combinations with an anti-CTLA-4 antibody, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) *J Clin Oncol* 28:3167-75). Thus, 0.3 mg/kg dosing can allow for sufficient exposure to lead to maximal biologic activity.

In some embodiments of the invention, the anti-PD-1 antibody is administered at a dose of 3 mg/kg. In other embodiments of the invention, the anti-PD-1 antibody is administered at a dose of 1 mg/kg.

In certain embodiments, the dose of an anti-PD-1 antibody (or an anti-PD-L1 antibody) is a fixed dose in a pharmaceutical composition. In other embodiments, the method of the present invention can be used with a flat dose (a dose given to a patient irrespective of the body weight of the patient). In embodiments, the flat dose of the anti-PD-1 antibody or antigen binding portion thereof is at least about 100 mg, 120 mg, 140 mg, 160 mg, 180 mg, 200 mg, 220 mg, 240 mg, 260 mg, 280 mg, 300 mg, 360 mg, 400 mg, 420 mg, 440 mg, 460 mg, 480 mg, 500 mg, 520 mg, 540 mg, 560 mg or 600 mg. For example, a flat dose of a nivolumab can be about 240 mg. For example, a flat dose of pembrolizumab can be about 200 mg. In embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In embodiments, the flat dose of the anti-PD-1 antibody or antigen binding portion thereof is administered once about every week, every two weeks, every three weeks, every four weeks, every five weeks, or every six weeks. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

Ipilimumab (YERVOY®) is approved for the treatment of melanoma at 3 mg/kg given intravenously once every 3 weeks for 4 doses. Thus, in some embodiments, about 3 mg/kg is the highest dosage of ipilimumab used in combination with the anti-PD-1 antibody though, in certain embodiments, the anti-CTLA-4 antibody such as ipilimumab can be dosed within the range of about 0.3 to about 10 mg/kg, about 0.5 to about 10 mg/kg, about 0.5 to about 5 mg/kg, about 1 to about 5 mg/kg, about 1 to about 4 mg/kg, or about 1 to about 3 mg/kg body weight about every two, three, four, five, six, seven, eight, nine, ten, eleven, twelve, thirteen, fourteen, fifteen or twenty weeks when combined with the anti-PD-1 antibody. In other embodiments, the anti-CTLA-4 antibody is administered on a different dosage schedule from the anti-PD-1 antibody. In some embodiments, ipilimumab is administered about every week, about every two weeks, about every three weeks, about every 4 weeks, about every five weeks, about every six weeks, about every seven weeks, about every eight weeks, about every nine weeks, about every ten weeks, about every eleven weeks, about every twelve weeks, about every thirteen weeks, about every fourteen weeks, about every fifteen weeks or about every twenty weeks. Dosages of ipilimumab that are lower than the typical 3 mg/kg, but not less than 0.001 mg/kg, are subtherapeutic dosages. The subtherapeutic doses of an anti-CTLA-4 antibody used in the methods herein are higher than 0.001 mg/kg and lower than 3 mg/kg. In some embodiments, the subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. It has been shown that combination dosing of nivolumab at 3 mg/kg and ipilimumab at 3 mg/kg exceeded the MTD in a melanoma population, whereas a combination of nivolumab at 1 mg/kg plus ipilimumab at 3 mg/kg or nivolumab at 3 mg/kg plus ipilimumab at 1 mg/kg was found to be tolerable in melanoma patients (Wolchok et al. (2013) *N Engl J Med* 369(2): 122-33). Accordingly, although nivolumab is tolerated up to 10 mg/kg given intravenously every 2 weeks, in certain embodiments doses of the anti-PD-1 antibody do not exceed about 3 mg/kg when combined with the anti-CTLA-4 antibody. In certain embodiments, the dosage of the anti-CTLA-4 antibody is about 1 mg/kg.

In certain embodiments, based on risk-benefit and PK-PD assessments, the dosage used comprises a combination of nivolumab at about 1 mg/kg plus ipilimumab at about 1 mg/kg or nivolumab at about 3 mg/kg plus ipilimumab at about 1 mg/kg, In some embodiments, nivolumab is administered at a dosing frequency of once about every 2 weeks. In certain embodiments, ipilimumab is administered at a dosing frequency of once about every six or twelve weeks. In certain other embodiments, nivolumab is administered at a dosage of about 1 or about 3 mg/kg in combination with ipilimumab administered at a dosage of about 1 mg/kg, with nivolumab administered every two weeks and ipilimumab administered every six weeks or every twelve weeks. In certain other embodiments, nivolumab is administered at a dosage of 1 mg/kg every two weeks in combination with ipilimumab administered at a dosage of about 1 mg/kg, every six weeks. In some embodiments, nivolumab is administered at a dosage of 1 mg/kg every two weeks in combination with ipilimumab administered at a dosage of about 1 mg/kg, every twelve weeks. In certain embodiments, nivolumab is administered at a dosage of 3 mg/kg every two weeks in combination with ipilimumab administered at a dosage of about 1 mg/kg, every six weeks. In other embodiments, nivolumab is administered at a dosage of 3 mg/kg every two weeks in combination with ipilimumab administered at a dosage of about 1 mg/kg, every twelve weeks.

In certain embodiments, the anti-PD-1 antibody and the anti-CTLA-4 antibody is formulated as a single composition, wherein the dose of the anti-PD-1 antibody and the dose of the anti-CTLA-4 antibody are combined in a fixed-dose at a ratio of 1:50, 1:40, 1:30, 1:20, 1:10. 1:5, 1:3, 1:1, 3:1, 5:1, 10:1, 20:1, 30:1, 40:1, or 50:1. In certain embodiments, the dose of the anti-CTLA-4 antibody is a flat dose, which is given to a patient irrespective of the body weight. In some embodiments, the flat dose of the anti-CTLA-4 antibody is at least about 40 mg, 50 mg, 60 mg, 70 mg, 80 mg, 90 mg, 100 mg, 120 mg, 140 mg, 160 mg, 180 mg or 200 mg. In a specific embodiment, the flat dose of the anti-CTLA-4 antibody is about 80 mg.

Dosage and frequency vary depending on the half-life of the antibody in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredients in the pharmaceutical compositions of the present invention can be varied so as to obtain an amount of the active ingredient that is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Kits

Also within the scope of the present invention are kits comprising an anti-PD-1 antibody and another anti-cancer agent for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a lung cancer, the kit comprising: (a) an amount ranging from about 4 mg to about 500 mg of a PD-1 antibody or an antigen-binding portion thereof; (b) an amount ranging from about 40 mg to about 500 mg of a CTLA-4 antibody or an antigen-binding portion thereof; and (c) instructions for using the PD-1 antibody or an antigen-binding portion thereof and the CTLA-4 antibody or an antigen-binding portion thereof in any method disclosed herein. In some embodiments, the kit contains the PD-1 antibody or an antigen-binding portion thereof and the CTLA-4 antibody or an antigen-binding portion thereof as separation compositions. In some embodiments, the kit contains the PD-1 antibody or an antigen-binding portion thereof and the CTLA-4 antibody or an antigen-binding portion thereof as a single composition. In certain embodiments, the anti-PD-1, and the anti-CTLA-4 antibody can be co-packaged in unit dosage form. In certain embodiments for treating human patients, the kit comprises an anti-human PD-1 antibody disclosed herein, e.g., nivolumab or pembrolizumab. In other embodiments, the kit comprises an anti-human CTLA-4 antibody disclosed herein, e.g., ipilimumab or tremelimumab.

The present invention is further illustrated by the following example that should not be construed as further limiting. The contents of all references cited throughout this application are expressly incorporated herein by reference.

Example 1

Treatment of NSCLC with Nivolumab and Ipilimumab

Study Design

Four different arms were developed to test dosages and dosing schedules of nivolumab ("nivo") and ipilimumab ("ipi"). These arms were designed to test different dosing schedules from the initial testing of the nivo+ipi combination treatment. An overview of the results of the previous combination treatments is seen in Table 1. NR=not reached.

TABLE 1

Previously Presented Cohorts with Advanced NSCLC. See Gettinger, S., et al. *J. Clin Oncol 33(suppl)*: 8025 (2015) and Antonia, S. J., et al. *Int. J. Radial Oncol Bio Phys 90(suppl 5)*: S32-S33 (2014).

|  | Nivo 3 mg/kg Q3W N = 52 | Nivo 1 mg/kg + Ipi 3 mg/kg Q3W N = 24 | Nivo 3 mg/kg + Ipi 1 mg/kg Q3W N = 25 |
|---|---|---|---|
| Confirmed ORR, % | 23 | 13 | 20 |
| Estimated mDOR, mos | NR | NR | NR |
| 1-year OS rate, % | 74 | 65 | 44 |
| Treatment-related AEs, % |  |  |  |
| Any grade | 71 | 92 | 84 |
| Grade 3-4 | 19 | 58 | 44 |
| Treatment-related AEs leading to discontination, % | 10 | 37 |  |
| Treatment related deaths, n | — | 3 |  |

The data for Nivo 3 mg/kg Q3 W is based on a March 2015 database lock. The data for Nivo 1 mg/kg+Ipi 3 mg/kg Q3 W and Nivo 3 mg/kg+Ipi 1 mg/kg Q3 Wis based on a on a September 2015 database lock. The estimated mDOR is the time from first response to documented progression, death within 100 days of last nivolumab dose, or last tumor assessment (for censored+data)

Four additional arms were tested: 1 mg/kg ipi and 1 mg/kg nivo q3w; 1 mg/kg nivo q2w and 1 mg/kg ipi q6w; 3 mg/kg nivo q2w and 1 mg/kg ipi q12w; 3 mg/kg nivo q2w and 1 mg/kg ipi q6w. The demographics, mutations, and baseline disease characteristics of the patients are shown in Table 2.

TABLE 2

Baseline characteristics of patients.

| | Nivo 1 + Ipi 1 Q3W N = 31 | Nivo 1 Q2W + Ipi 1 Q6W N = 40 | Nivo 3 Q2W + Ipi 1 Q12W N = 38 | Nivo 3 Q2W + Ipi 1 Q6W N = 39 |
|---|---|---|---|---|
| Age | | | | |
| Median, yrs (range) | 63 (37, 83) | 65 (38, 85) | 68 (50, 91) | 62 (47, 87) |
| ≥65, % | 42 | 53 | 55 | 46 |
| Male, % | 48 | 45 | 45 | 62 |
| ECOG PS, % | | | | |
| 0 | 35 | 35 | 32 | 41 |
| 1 | 61 | 65 | 68 | 54 |
| Not reported | 3 | 0 | 0 | 5 |
| Smoking status, % | | | | |
| Never | 26 | 28 | 5 | 23 |
| Former/current | 74 | 73 | 95 | 74 |
| Unknown | 0 | 0 | 0 | 3 |
| Disease Stage | | | | |
| Stage IIIB | 13 | 5 | 11 | 3 |
| Stage IV | 87 | 95 | 89 | 97 |
| Histology | | | | |
| Nonsquamous | 81 | 80 | 82 | 85 |
| Squamous | 19 | 20 | 18 | 15 |
| EGFR mutation status | | | | |
| Positive | 16 | 5 | 11 | 10 |
| Negative | 68 | 83 | 74 | 67 |
| Unknown | 16 | 13 | 16 | 23 |
| PD-L1 expression, % | 81 | 70 | 82 | 77 |
| ≥1% | 48 | 75 | 68 | 77 |
| ≥5% | | | 52 | 63 |
| ≥10% | | | 42 | 50 |
| ≥25% | | | 32 | 27 |
| ≥50% | | | 19 | 23 |
| ≤1% | 52 | 25 | | |
| PD-L1 unknown | 19 | 30 | 18% | 23% |

Some percentages may not total 100% due to rounding. The PD-L1 expression percentages are based on patients with known PD-L1 status (nivo 1 + ipi 1 Q3W, n = 25; nivo 1 Q2W + ipi 1 Q6W, n = 28; nivo 3 Q2W + ipi 1 Q12W, n = 31; nivo 3 Q2W + ipi Q6W, n = 30)

The most common treatment-related adverse events (AE) are seen in Table 3. At the time of the analyses, 47%-81% of patients (across the arms) had discontinued study treatment, most commonly due to progressive disease.

TABLE 3

Safety Summary, Exposure and Patient Disposition

|  | Nivo 1 + Ipi Q3W N = 31 | | Nivo 1 Q2W + Ipi 1 Q6W N = 40 | | Nivo 3 Q2W + Ipi 1 Q12W N = 38 | | Nivo 3 Q2W + Ipi 1 Q6W N = 39 | |
| --- | --- | --- | --- | --- | --- | --- | --- | --- |
|  | Any grade | Grade 3-4 | Any grade | Grade 3-4 | Any grade | Grade 3-4 | Any grade | Grade 3-4 |
| Treatment-related AEs, % | 77 | 29 | 73 | 35 | 74 | 29 | 69 | 28 |
| Treatment-related AEs leading to discontinuation, % | 13 | 10[1] | 8 | 8[2] | 5 | 3[3] | 10 | 10[4] |
| Median number of doses, n(range) | | | | | | | | |
| Nivolumab | 4 (1-42) | | 7 (1-26) | | 13 (1-26) | | 8 (1-25) | |
| Ipilimumab | NC (1-4)[5] | | 3 (1-9) | | 3 (1-5) | | 2 (1-9) | |
| Median duration of therapy, weeks (range) | | | | | | | | |
| Nivolumab | 12.0 (3.0-92.0) | | 16.0 (2.0-59.0) | | 28.7 (2.0-52.0) | | 18.0 (2.0-53.0) | |
| Ipilimumab | 11.6 (3.0-24.0) | | 17.6 (6.0-59.0) | | 35.7 (12.0-60.0) | | 15.0 (6.0-54.0) | |
| Patients not continuing treatment, % | 81 | | 65 | | 47 | | 62 | |
| Progressive Disease | 58 | | 40 | | 26 | | 38 | |
| Study drug toxicity | 16 | | 8 | | 5 | | 8 | |
| Other | 3 | | 3 | | 3 | | 5 | |
| Patient withdrew consent | 0 | | 8 | | 3 | | 0 | |
| Death | 0 | | 3 | | 5 | | 3 | |
| AE unrelated to study drug | 0 | | 0 | | 5 | | 5 | |
| Patient request to discontinue treatment | 0 | | 5 | | 0 | | 3 | |
| Patient no longer meets study criteria | 3 | | 0 | | 0 | | 0 | |

[1]Increased aspartate aminotransferase, rash and pneumonitis (n = 1 each).
[2]Autoimmune hepatitis (=2), increased alanine aminotransferase and increased AST (n = 1 each).
[3]Colitis (n = 1).
[4]Increased transaminase, encephalopathy, facial nerve disorder, rash and pneumonitis (n = 1 each).
NC = not calculated. The treatment-related adverse events were less frequent and less severe with the new dosing schedules in comparison to the early nivolumab plus ipilimumab cohorts (seen in Table 1). The new dosing schedules were associated with a low frequency of treatment-related adverse events leading to discontinuation (Table 3) in comparison to early nivolumab plus ipilimumab cohorts. The discontinuation rates were comparable to nivolumab monotherapy (seen in Table 1). There were no treatment-related deaths.
[5]Median number of ipilimumab doses was NC, as patients received a maximum of 4 doses.

Select treatment-related adverse events can be seen in Table 4. Select adverse events are those with potential immunologic etiology that require frequent monitoring/intervention. Across arms, the most common categories of treatment-related select adverse events (any grade≥20%) were: skin, endocrine, gastrointestinal, and hepatic.

TABLE 4

Treatment-related select AEs reported in patients treated with nivolumab plus ipilimumab.

|  | Nivo 1 + Ipi Q3W N = 31 | | Nivo 1 Q2W + Ipi 1 Q6W N = 40 | | Nivo 3 Q2W + Ipi 1 Q12W N = 38 | | Nivo 3 Q2W + Ipi 1 Q6W N = 39 | |
| --- | --- | --- | --- | --- | --- | --- | --- | --- |
| Select AE category, % | Any grade | Grade 3-4 | Any grade | Grade 3-4 | Any grade | Grade 3-4 | Any grade | Grade 3-4 |
| Skin | 48 | 13 | 33 | 5 | 39 | 3 | 31 | 5 |
| Gastrointestinal | 19 | 0 | 28 | 8 | 18 | 5 | 26 | 5 |
| Endocrine | 13 | 6 | 30 | 8 | 8 | 3 | 21 | 5 |

TABLE 4-continued

Treatment-related select AEs reported in patients treated with nivolumab plus ipilimumab.

| Select AE category, % | Nivo 1 + Ipi Q3W N = 31 | | Nivo 1 Q2W + Ipi 1 Q6W N = 40 | | Nivo 3 Q2W + Ipi 1 Q12W N = 38 | | Nivo 3 Q2W + Ipi 1 Q6W N = 39 | |
|---|---|---|---|---|---|---|---|---|
| | Any grade | Grade 3-4 | Any grade | Grade 3-4 | Any grade | Grade 3-4 | Any grade | Grade 3-4 |
| Hepatic | 10 | 6 | 23 | 10 | 3 | 0 | 5 | 5 |
| Pulmonary[6] | 10 | 3 | 8 | 0 | 5 | 3 | 3 | 3 |
| Renal | 0 | 0 | 3 | 0 | 8 | 5 | 5 | 0 |
| Hypersensitivity/infusion reaction | 0 | 0 | 3 | 0 | 5 | 0 | 0 | 0 |

[6]All treatment-related pulmonary events were pneumonitis.

All treatment-related pulmonary events were pneumonitis.

The overall response, progression-free survival and overall survival summary is in Table 5. The confirmed overall response rates (ORRs) ranged from 13%-39% across all arms, with a further 21-42% of patients achieving stable disease. Two patients in the arm nivolumab 3 mg/kg Q2 W+ipilimumab 1 mg/kg Q12 W and one patient in the arm nivolumab 3 mg/kg Q2 W+ipilimumab 1 mg/kg Q6 W had an unconventional immune response, with 42%, 47%, and 44% maximum reductions in target lesions following progressive disease or simultaneous appearance of new lesions. Median DOR was not reached in any arm. Reductions in tumor burden were observed across all of the arms (FIGS. 2A-2D). Surprisingly, nivolumab at 3 mg/kg Q2 W plus ipilimumab at 1 mg/kg Q12 W and nivolumab at 3 mg/kg Q2 W plus ipilimumab at 1 mg/kg Q6 W showed significant increases in patients who had a complete response as well as the length of progressive free survival in comparison to nivolumab 1 mg/kg Q2 W plus ipilimumab 1 mg/kg Q6 W.

TABLE 5

Response Summary (August 2015 database lock, except where otherwise noted).

| | Nivo 1 + Ipi 1 Q3W N = 31 | Nivo 1 Q2W + Ipi 1 Q6W N = 40 | Nivo 3 Q2W + Ipi 1 Q12W N = 38 | Nivo 3 Q2W + Ipi 1 Q6W N = 39 |
|---|---|---|---|---|
| Confirmed ORR, % (95% CI) | 13 (4, 30) | 25 (13, 41) | 47[7] (31, 64) | 39[7] (23, 55) |
| Median duration of response, mo (95% CI)[7] | | | NR (11.3, NR) | NR (8.4, NR) |
| DCR, % (95% CI) | 55 (36, 73) | 58 (41, 73) | 74 (57, 87) | 51 (35, 68) |
| Best overall response, % | | | | |
| Complete Response (CR) | 0 | 0 | 0[7] | 0[7] |
| Partial Response (PR) | 13 | 25 | 47[7] | 39[7] |
| Unconfirmed PR | 3 | 3 | | |
| Stable disease (SD) | 42 | 33 | 32[7] | 181[7] |
| Progressive disease (SD) | 35 | 30 | 13[7] | 28[7] |
| Unable to determine | 6 | 10 | 8[7] | 15[7] |
| mPFS, mos (95% CI) | 10.6 (2.1, 16.3) | 4.9 (2.8,) | 8.1[7] (5.6, 13.6,) | 3.9[7] (2.6, 13.2) |
| PFS rate at 24 weeks, % (95% CI) | 55 (36.1, 71) | NC | 63 (44, 76) | NC |
| mOS, mos (95% CI) | NR (11.5,) | NR (8.9,) | NR | NR (8.7,) |
| 1-year OS rate, % (95% CI)[7] | | | NC | 69 (52, 81) |
| Median follow-up, mos (range) | 16.6 (1.8-24.5) | 6.2 (0.4-13.1) | 12.9[7] (0.9-18.0) | 11.8[7] (1.1-18.2) (1.1-12.2) |

NC = not calculated (when >25% of patients are censored);

NR = not reached NR due to high percentage of ongoing response or insufficient number of events and/or follow-up.

Symbol + indicates a censored value.

DCR = disease control rate;

mOS = median OS;

mPFS = median PFS.

The DCR includes patients with confirmed CR, PR and SD.

[7]February 2016 database lock

Figure 4:
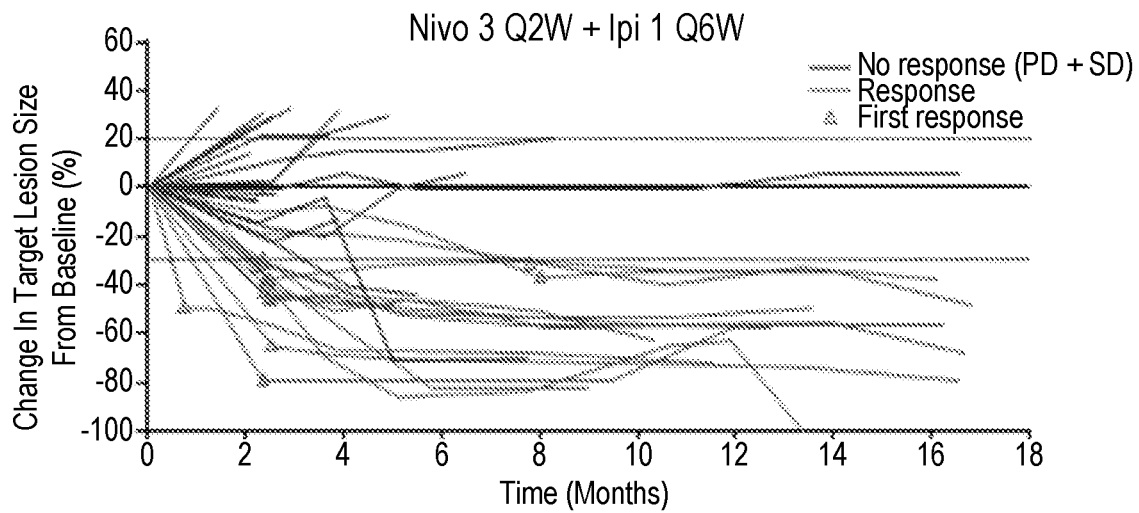
FIG. 4 shows the duration of response of nivo+ipi in first line NSCLC.

The duration of response of nivo plus ipi in first-line NSCLC can be seen in FIG. 4. 12 of 15 responders (80%) in the Q6 W arm and 14 of 18 responders (77%) in the Q12 W arm had a response documented by the time of first scan in week 11+/−5 days. 12 of 15 responders (80%) and 12 of 18 responders (67%) had an ongoing response in the Q6 W and Q12 W arms, respectively, at the time of database lock.

Figure 3:
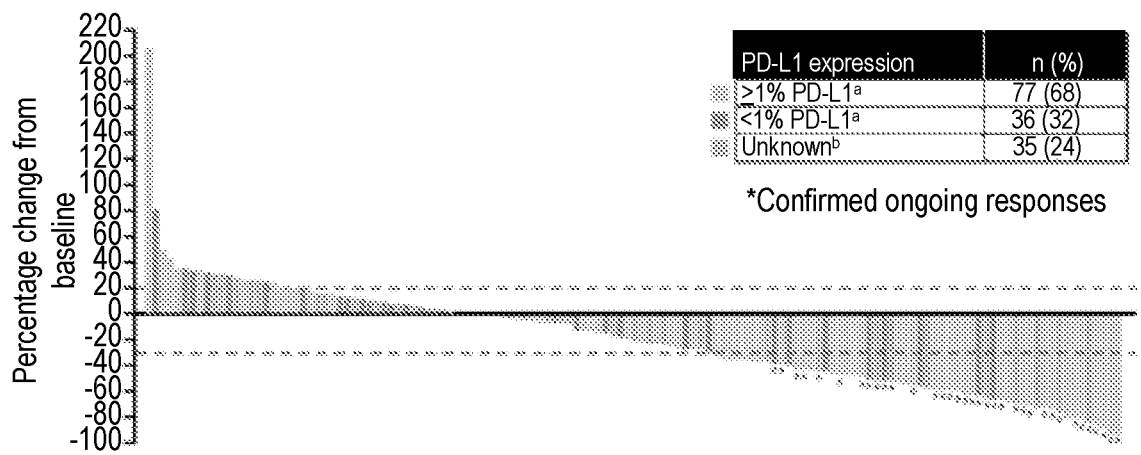
FIG. 3 shows the best percentage change in target lesion tumor burden by baseline tumor PD-L1 expression.
Figure 5:
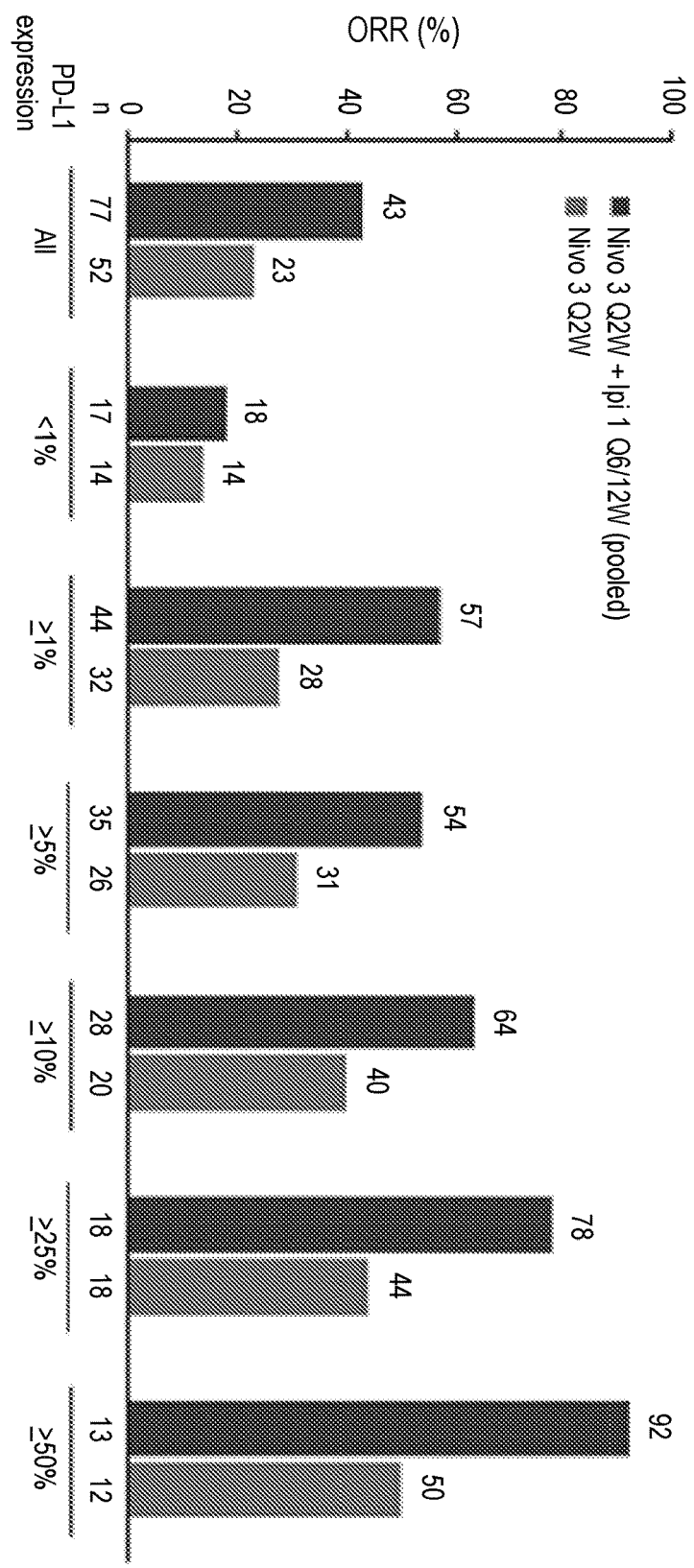
FIG. 5 shows the efficacy of nivo+ipi across all tumor PD-L1 expression levels.

The efficacy of the treatments by baseline tumor PD-L1 expression can be seen in Table 6. Tumor PD-L1 expression was assessed in pretreatment (archival or fresh) tumor samples using the automated Bristol-Myers Squibb/Dako immunohistochemistry assay, and evaluated for ORR and PFS. See Phillips, T. et al. *Appl. Immunohistochem Mol Morphol* 23: 541-549 (2015) All patients had available pretreatment tumor samples, 76% (113/148) had samples evaluable for PD-L1 expression. Furthermore, clinical activity was observed regardless of tumor PD-L1 expression (FIG. 3), but there is preliminary evidence of greater activity in ≥1% PD-L1 expressing tumors. 85% (35/41) of confirmed responses were ongoing at the time of analysis. Median DOR was not reached in any arm, regardless of tumor PD-L1 expression. A further evaluation can be seen in Table 7, and the efficacy of nivo plus ipi across PD-L1 expression levels can be seen in FIG. 5.

Figure 6A:
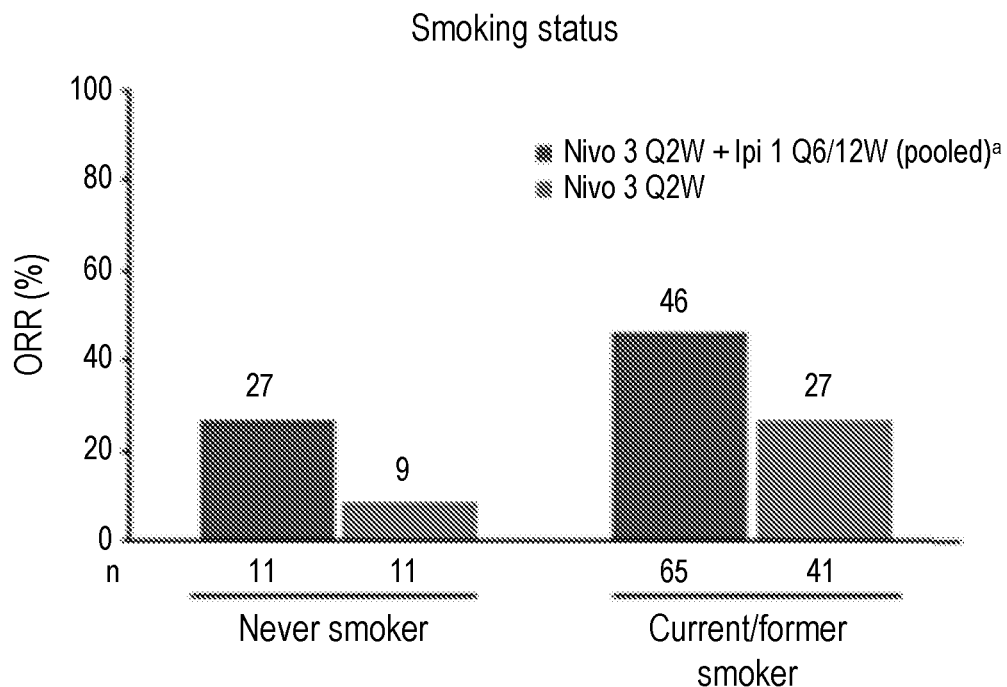
FIGS. 6A and 6B show the efficacy of nivo+ipi in first line NSCLC by smoking (FIG. 6A) and EGFR mutation (FIG. 6B) status.
Figure 6B:
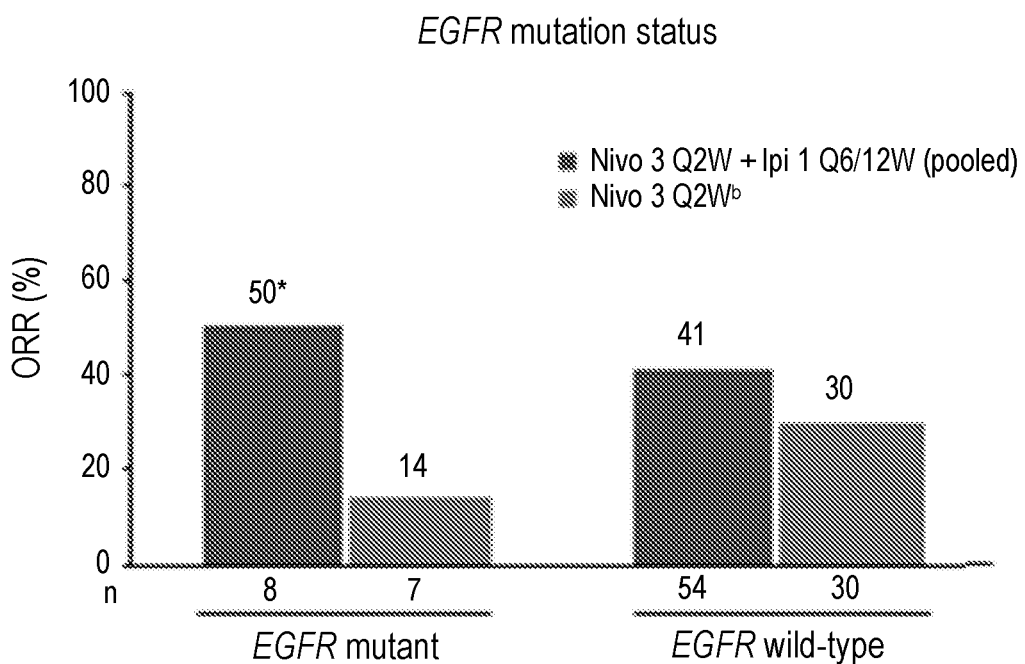

8 and FIG. 6A. Among patients with non-squamous NSCLC, responses were observed regardless of EGFR mutation status. See Table 9 and FIG. 6B. These data evidence that clinical activity was observed regardless of smoking status or EGFR mutation status.

TABLE 8

Efficacy by smoking status in patients treated with nivolumab plus ipilimumab.

| | Nivo + Ipi | | |
| --- | --- | --- | --- |
| Smoking Status | Current N = 19 | Former N = 98 | Never N = 30 |
| ORR, % | 26 | 32 | 17 |
| mPFS, mos (95% CI) | 8.0 (3.6,) | 7.8 (3.7, 11.2) | 3.7 (2.3, 12.1) |

TABLE 6

Efficacy by baseline tumor PD-L1 expression

| | Nivo 1 + Ipi 1 Q3W N = 31 | | Nivo 1 Q2W + Ipi 1 Q6W N = 40 | | Nivo 3 Q2W + Ipi 1 Q12W N = 38 | | Nivo 3 Q2W + Ipi 1 Q6W N = 39 | |
| --- | --- | --- | --- | --- | --- | --- | --- | --- |
| PD-L1 expression | ≥1% PD-L1 (n = 12) | <1% PD-L1 (n = 13) | ≥1% PD-L1 (n = 21) | <1% PD-L1 (n = 7) | ≥1% PD-L1 (n = 21) | <1% PD-L1 (n = 9) | ≥1% PD-L1 (n = 23) | <1% PD-L1 (n = 7) |
| ORR, % | 8 | 15 | 24 | 14 | 48 | 22 | 48 | 0 |
| mPFS, mos | 2.6 | 7.8 | 4.9 | NR | 8.0 | 5.3 | NR | 2.4 |
| (95% CI) | (1.6,) | (2.0,) | (2.6,) | (2.3,) | (3.6, 8.1) | (0.9,) | (3.5,) | (1.7, 2.9) |
| PFS rate at 24 weeks, % | 42 | 57 | 40 | NC | 74 | 39 | 65 | 0 |
| (95% CI) | (15, 67) | (25, 80) | (18, 61) | | (48, 88) | (9. 69) | (41, 81) | 0 |

NR due to a high percentage of ongoing response or inefficiency number of events and/or follow-up.

TABLE 7

Efficacy by baseline tumor PD-L1 expression

| | Nivo 3 Q2W + Ipi 1 Q12W | Nivo 3 Q2W + Ipi 1 Q6W | Nivo 3 Q2W |
| --- | --- | --- | --- |
| ORR, % (n/N) | | | |
| <1% PD-L1 | 30 (3/10) | 0 (0/7) | 14 (2/14) |
| ≥1% PD-L1 | 57 (12/21) | 57 (13/23) | 28 (9/32) |
| ≥50% PD-L1 | 100 (6/6) | 86 (6/7) | 50 (6/12) |
| Median PFS (95% CI), mo | | | |
| <1% PD-L1 | 4.7 (0.9, NR) | 2.4 (1.7, 2.9) | 6.6 (2.0, 11.2) |
| ≥1% PD-L1 | 8.1 (5.6, NR) | 10.6 (3.6, NR) | 3.5 (2.2, 6.6) |
| ≥50% PD-L1 | 13.6 (6.4, NR) | NR (7.8, NR) | 8.4 (2.2, NR) |
| 1-year OS rate (95% CI), % | | | |
| <1% PD-L1 | NC | NC | 69 (50, 82) |
| ≥1% PD-L1 | 90 (66, 97) | 83 (60, 93) | 79 (47, 93) |
| ≥50% PD-L1 | NC | 100 (100, 100) | 83 (48, 96) |

The median PFS and the overall response rate (ORR) were higher among current and former smokers. See Table

TABLE 9

Efficacy by EGFR mutation status in non-squamous patients treated with nivolumb plus ipilimumab

| | Nivo + Ipi | |
| --- | --- | --- |
| | EGFR Mut N = 19 | EGFR WT N = 78 |
| Confirmed ORR, % (95% CI) | 33 (8, 70) | 32 (22, 44) |
| DCR, % (95% CI) | 44 (14, 79) | 63 (51, 74) |
| mDOR, mos (range) | NR (3.0+-5.6+) | NR (0.9+-8.3+) |
| mPFS, mos (95% CI) | NR (8.1,) | 24.1 (15.9, 35.3) |
| PFS rate at 24 weeks, % (95% CI) | NC | 51 (38, 62) |
| mOS, mos (95% CI) | NR (1.9,) | NR |

NR due to high percentage of ongoing response or insufficient number of events and/or follow-up. Symbol + indicates a censored value. These values include patients with non-squamous histology who were treated with nivo 1 mg/kg Q2W + ipi 1 mg/kg Q6W, nivo 3 mg/kg Q2W + ipi 1 mg/kg Q12W or nivo 3 mg/kg Q2W + ipi 1 mg/kg Q6W. The DCR includes patients with confirmed complete response, partial response, and stable disease. Symbol + indicates a censored value.

Conclusions

Although early studies with 1 mg/kg nivolumab and 3 mg/kg ipilimumab or 3 mg/kg nivolumab and 1 m/kg ipilimumab every three weeks showed clinical activity, the dosing schedules were associated with toxicity. In this study, new dosing schedules have demonstrated unexpectedly synergistic activity and increased clinical activity, as well as acceptable safety. First-line therapy with nivolumab plus ipilimumab demonstrates a high level of clinical activity that is characterized by deep and durable responses in patients with advanced NSCLC. Furthermore, treatment with a combination of nivolumab plus ipilimumab is associated with a favorable safety profile. There was a low frequency of treatment-related grade 3-4 adverse events leading to discontinuation, and no treatment related deaths.

Example 2

Case of Pathological CR in One Patient Receiving Nivo 3 Q2 W+Ipi 1 Q6 W

A 54-yr male (former smoker, 52 pack-yrs) with metastatic large-cell lung cancer (PD-L1<1%; Patient was included as having partial response and PD-L1 expression unknown in analysis at time of database lock) was treated with Nivo 3 Q2 W+Ipi 1 Q6 W. The patient had a 53% total tumor size reduction by RECIST, and radiographic residual lesions in the lung and mediastinal lymph nodes, without distant disease. See FIGS. 7A-7D.

Embodiments

E1. A method for treating a subject afflicted with a lung cancer comprising administering to the subject a combination of:
 (a) an antibody or an antigen-binding portion thereof that binds specifically to a Programmed Death-1 (PD-1) receptor and inhibits PD-1 activity, wherein the PD-1 antibody or an antigen-binding portion thereof is administered at a dose ranging from about 0.1 to about 5.0 mg/kg body weight once about every two weeks; and
 (b) an antibody or an antigen-binding portion thereof that binds specifically to Cytotoxic T-Lymphocyte Antigen-4 (CTLA-4) and inhibits CTLA-4 activity, wherein the CTLA-4 antibody or an antigen-binding portion thereof is administered at a dose ranging from about 1 to about 5.0 mg/kg body weight once about every six or twelve weeks.

E2. The method of E1, wherein the lung cancer is non-small cell lung cancer (NSCLC).

E3. The method of E2, wherein the NSCLC has a squamous histology.

E4. The method of E2, wherein the NSCLC has a non-squamous histology.

E5. The method of any one of E1-4, wherein the anti-PD-1 antibody or antigen-binding portion thereof cross-competes with nivolumab for binding to human PD-1.

E6. The method of any one of E1-5, wherein the anti-PD-1 antibody or antigen-binding portion thereof is a chimeric, humanized or human monoclonal antibody or a portion thereof.

E7. The method of any one of E1-E6, wherein the anti-PD-1 antibody or antigen-binding portion thereof comprises a heavy chain constant region which is of a human IgG1 or IgG4 isotype.

E8. The method of any one of E1-E7, wherein the anti-PD-1 antibody is nivolumab.

E9. The method of any one of E1-E7, wherein the anti-PD-1 antibody is pembrolizumab.

E10. The method of any one of E1-E9, wherein the anti-CTLA-4 antibody or antigen-binding portion thereof is a chimeric, humanized or human monoclonal antibody or a portion thereof.

E11. The method of any one of E1-E10, wherein the anti-CTLA-4 antibody or antigen-binding portion thereof comprises a heavy chain constant region which is of a human IgG1 isotype.

E12. The method of any one of E1-E11, wherein the anti-CTLA-4 antibody is ipilimumab.

E13. The method of any one of E1-E11, wherein the anti-CTLA-4 antibody is tremelimumab.

E14. The method of any one of E1-E13, wherein the anti-CTLA-4 antibody or antigen-binding portion thereof cross-competes with ipilimumab for binding to human CTLA-4.

E15. The method of any one of E1-14, wherein the anti-PD-1 antibody or antigen-binding portion thereof is administered at a dose of about 1 mg/kg or about 3 mg/kg body weight once about every 2 weeks.

E16. The method of any one of E1-E15, wherein the anti-CTLA-4 antibody or antigen-binding portion thereof is administered at a dose of about 1 mg/kg body weight.

E17. The method of any one of E1-E16, wherein the anti-PD-1 antibody or antigen-binding portion thereof is administered at a dose of about 3 mg/kg body weight once about every 2 weeks and the anti-CTLA-4 antibody or antigen-binding portion thereof is administered at a dose of about 1 mg/kg body weight once about every 12 weeks.

E18. The method of any one of E1-E16, wherein the anti-PD-1 antibody or antigen-binding portion thereof is administered at a dose of about 1 mg/kg body weight once about every 2 weeks and the anti-CTLA-4 antibody or antigen-binding portion thereof is administered at a dose of about 1 mg/kg body weight once about every 6 weeks.

E19. The method of any one of E1-E18, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E20. The method of E19, wherein the subject exhibits progression-free survival of at least about eight months after the initial administration.

E21. The method of any one of E1-E20, wherein the subject has a longer progression-free survival when the subject is treated with an anti-PD-1 antibody or antigen-binding portion thereof administered at a dose of about 3 mg/kg body weight once about every 2 weeks and an anti-CTLA-4 antibody or antigen-binding portion thereof administered at a dose of about 1 mg/kg body weight once about every 12 weeks ("regimen A") than when the subject is treated with an anti-PD-1 antibody or antigen-binding portion thereof administered at a dose of 1 mg/kg body weight once every 2 weeks and an anti-CTLA-4 antibody or antigen-binding portion thereof administered at a dose of 1 mg/kg body weight every 6 weeks ("regimen B").

E22. The method of E21, wherein the progression-free survival of a subject administered regimen A is at least about 1 week, at least about 2 weeks, at least about 3 weeks, at least about 1 month, at least about 2 months, at least about 3 months, at least about 4 months, at least about 5 months or at least about six months longer than the progression-free survival of a subject administered regimen B.

E23. The method of E21 or E22, wherein the progression-free survival of a subject administered regimen A is at least about 3 months longer than the progression-free survival of a subject administered regimen B.

E24. The method of any one of E1-E22, wherein the subject has a longer progression-free survival when subject is treated with an anti-PD-1 antibody or antigen-binding portion thereof administered at a dose of 3 mg/kg body weight once every 2 weeks and an anti-CTLA-4 antibody or antigen-binding portion thereof administered at a dose of 1 mg/kg body weight every 12 weeks ("regimen A") than when the subject is treated with an anti-PD-1 antibody or antigen-binding portion thereof administered at a dose of 3 mg/kg body weight once every 2 weeks ("regimen C").

E25. The method of E23, wherein the progression-free survival of a subject administered regimen A is at least about 1 week, at least about 2 weeks, at least about 3 weeks, at least about 4 weeks, at least about 5 weeks, at least about 6 weeks, at least about 7 weeks, at least about 8 weeks, at least about 9 week, at least about 10 weeks, at least about 11 weeks, at least about 12 weeks, at least about 13 weeks, at least about 14 weeks, or at least about 15 weeks longer than the progression-free survival of a subject administered regimen C.

E26. The method of E21 or E22, wherein the progression-free survival of subjects administered regimen A is at least about 3 months longer than the progression-free survival of subjects administered regimen C.

E27. The method of any one of E1-E26, wherein the subject has a lung tumor that has ≥1% PD-L1, ≥5% PD-L1, ≥10% PD-L1, ≥25% PD-L1, or ≥50% PD-L1 expression.

E28. The method of any one of E1-E27, wherein the combination is administered for as long as clinical benefit is observed or until disease progression or unmanageable toxicity occurs.

E29. The method of any one of E1-E28, wherein the anti-PD-1 and anti-CTLA-4 antibodies are formulated for intravenous administration.

E30. The method of any one of E1-29, wherein the anti-PD-1 antibody or antigen-binding portion thereof and the anti-CTLA-4 antibody or antigen-binding portion thereof are administered sequentially to the subject.

E31. The method of any one of E1-30, wherein the anti-PD-1 and anti-CTLA-4 antibodies are administered within 30 minutes of each other.

E32. The method of any one of E1-E31, wherein the anti-PD-1 antibody or antigen-binding portion thereof is administered before the anti-CTLA-4 antibody or antigen-binding portion thereof.

E33. The method of any one of E1-E31, wherein the anti-CTLA-4 antibody or antigen-binding portion thereof is administered before the anti-PD-1 antibody or antigen-binding portion thereof.

E34. The method of any one of E1-E29, wherein the anti-PD-1 antibody or antigen-binding portion thereof and the anti-CTLA-4 antibody or antigen-binding portion thereof are administered concurrently in separate compositions.

E35. The method of any one of E1-E29, wherein the anti-PD-1 antibody or antigen-binding portion thereof and the anti-CTLA-4 antibody or antigen-binding portion thereof are administered concurrently as a single composition.

E36. The method of any one of E1-E35, wherein the anti-PD-1 antibody or antigen-binding portion thereof is administered at a subtherapeutic dose.

E37. The method of any one of E1-36, wherein the anti-CTLA-4 antibody or antigen-binding portion thereof is administered at a subtherapeutic dose.

E38. The method of any one of E1-E37, wherein the anti-PD-1 antibody or antigen-binding portion thereof and the anti-CTLA-4 antibody or antigen-binding portion thereof are each administered at a subtherapeutic dose.

E39. A kit for treating a subject afflicted with a lung cancer, the kit comprising:
(a) an amount ranging from about 4 mg to about 500 mg of an anti-PD-1 antibody or an antigen-binding portion thereof;
(b) an amount ranging from about 40 mg to about 500 mg of a CTLA-4 antibody or an antigen-binding portion thereof; and
(c) instructions for using the PD-1 antibody or an antigen-binding portion thereof and the CTLA-4 antibody or an antigen-binding portion thereof in the method of any of E1-E38.

What is claimed is:

1. A method of treating a subject afflicted with a lung cancer, comprising administering an antibody or an antigen-binding portion thereof that binds specifically to a Programmed Death-1 (PD-1) receptor and inhibits PD-1 activity ("anti-PD-1 antibody") and an antibody or an antigen-binding portion thereof that binds specifically to Cytotoxic T-Lymphocyte Antigen-4 (CTLA-4) and inhibits CTLA-4 activity ("anti-CTLA-4 antibody");
wherein at least 50% tumor cells of the lung cancer express PD-L1; and
wherein the anti-PD-1 antibody is administered at a dose of about 3 mg/kg body weight once about every 2 weeks and the anti-CTLA-4 antibody is administered at a dose of about 1 mg/kg body weight once about every 6 weeks.

2. The method of claim 1, wherein the lung cancer is non-small cell lung cancer (NSCLC).

3. The method of claim 1, wherein the anti-PD-1 antibody is nivolumab.

4. The method of claim 1, wherein the anti-CTLA-4 antibody is ipilimumab.

5. The method of claim 1, wherein the anti-PD-1 antibody is nivolumab and the anti-CTLA-4 antibody is ipilimumab.

6. The method of claim 1, wherein the anti-PD-1 antibody and the anti-CTLA-4 antibody are administered for as long as clinical benefit is observed or until disease progression or unmanageable toxicity occurs.

7. The method of claim 1, wherein the anti-PD-1 antibody and anti-CTLA-4 antibody are administered intravenously.

8. The method of claim 1, wherein the anti-PD-1 antibody and the anti-CTLA-4 antibody are administered sequentially to the subject.

9. The method of claim 1, wherein the anti-PD-1 antibody and the anti-CTLA-4 antibody are administered concurrently in separate compositions.

10. The method of claim 1, wherein the anti-PD-1 antibody and the anti-CTLA-4 antibody are administered concurrently as a single composition.

11. A method of treating a subject afflicted with a non-small cell lung cancer (NSCLC), comprising administering about 3 mg/kg body weight of nivolumab once about every 2 weeks and 1 mg/kg body weight of ipilimumab once every 6 weeks, wherein at least 50% tumor cells of the lung cancer express PD-L1.

* * * * *